(12) United States Patent
Abdulhamid

(10) Patent No.: US 12,146,101 B1
(45) Date of Patent: Nov. 19, 2024

(54) METHOD OF ENHANCING OIL RECOVERY USING CITRIC ACID-BASED ADDITIVE

(71) Applicant: KING FAHD UNIVERSITY OF PETROLEUM AND MINERALS, Dhahran (SA)

(72) Inventor: Mahmoud Atef Abdulhamid, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/339,274

(22) Filed: Jun. 22, 2023

(51) Int. Cl.
| | |
|---|---|
| *E21B 43/20* | (2006.01) |
| *C07C 231/02* | (2006.01) |
| *C09K 8/514* | (2006.01) |
| *C09K 8/584* | (2006.01) |
| *C09K 8/588* | (2006.01) |

(52) U.S. Cl.
CPC .......... *C09K 8/584* (2013.01); *C07C 231/02* (2013.01); *C09K 8/514* (2013.01); *C09K 8/588* (2013.01); *E21B 43/20* (2013.01); *C09K 2208/12* (2013.01)

(58) Field of Classification Search
CPC ........ C09K 8/584; C09K 8/514; C09K 8/588; C09K 2208/12; C07C 231/02; E21B 43/20
See application file for complete search history.

(56) References Cited

U.S. PATENT DOCUMENTS

| | | | |
|---|---|---|---|
| 9,732,268 B2 * | 8/2017 | Li | C09K 8/68 |
| 9,920,239 B2 * | 3/2018 | Xu | C09K 8/72 |
| 10,836,952 B2 | 11/2020 | Haq et al. | |
| 11,555,143 B2 | 1/2023 | Hussain et al. | |
| 2017/0247603 A1 * | 8/2017 | Perez-Regalado | C09K 8/584 |
| 2019/0256458 A1 * | 8/2019 | Hussain | C07C 237/16 |
| 2022/0162498 A1 | 5/2022 | Recio, III et al. | |
| 2022/0162929 A1 | 5/2022 | Recio, III et al. | |

OTHER PUBLICATIONS

M. Boussa, et al., "Production Optimization of Oil Wells (the Problem of Salt Deposits)", Journal of Canadian Petroleum Technology, vol. 44, Issue 5, May 1, 2005, 8 pages (Abstract only).
Fei Yang, et al., "Multi-alkylated aromatic amides amphiphiles effectively stabilize the associated asphaltene particles in crude oil", Journal of Petroleum Science and Engineering, vol. 212, Article 110204, May 2022, 6 pages (Abstract only).

* cited by examiner

*Primary Examiner* — Silvana C Runyan

(74) *Attorney, Agent, or Firm* — Oblon, McClelland, Maier & Neustadt, L.L.P.

(57) ABSTRACT

A method of enhancing oil recovery from a carbonate reservoir containing a hydrocarbon mixture includes injecting the carbonate reservoir with a sea-water solution comprising a citric acid-based additive to displace the hydrocarbon mixture from the carbonate reservoir thereby forming a hydrocarbon mixture containing sea-water mixture; and separating the hydrocarbon mixture from the hydrocarbon mixture containing sea-water mixture to recover the hydrocarbon mixture. The citric acid-based additive is present in the sea-water solution at a concentration of 1 to 1000 parts per million based on a total number of parts by weight of the sea-water solution. Particles of the citric acid-based additive are adsorbed on surfaces of the carbonate rocks in the carbonate reservoir.

20 Claims, 12 Drawing Sheets

METHOD OF ENHANCING OIL RECOVERY USING CITRIC ACID-BASED ADDITIVE

STATEMENT REGARDING PRIOR DISCLOSURE BY THE INVENTORS

Aspects of this technology are described in "Citric acid-based N-alkyl amides for enhanced oil recovery application in the carbonate reservoir: Sustainable laboratory-scale synthesis and recovery performance" published in Fuel, January 2023, which is incorporated herein by reference in its entirety.

STATEMENT OF ACKNOWLEDGEMENT

This research was supported by the College of Petroleum Engineering and Geoscience at King Fahd University of Petroleum and Minerals under the project SF21012.

BACKGROUND

Technical Field

The present disclosure is directed to a method of enhancing oil recovery from a carbonate reservoir containing a hydrocarbon mixture, more particularly, to a method of enhancing the oil recovery from the carbonate reservoir containing the hydrocarbon mixture using a citric acid-based additive.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The global demand for oil and gas has consistently risen in the past two decades due to industrial development and population growth. At the same time, most oilfield reserves are reaching their maturation stage. Therefore, it has become crucial to employ advanced techniques to increase production. Approximately 60% of the world's reservoirs are reported as highly complex and consist of carbonate formations with oil-wet characteristics [Akbar et al., Oilf. Rev. 12, 20-41, 2000; Nilsson et al., Colloids Surfaces A Physicochem. Eng. Asp. 127, 241-247, 1997]. Moreover, the reservoir condition of these formations is exceptionally harsh, with a temperature of more than 100° C., and a salinity of about 240,000 ppm containing a vast number of divalent ions ($Mg^{2+}$ and $Ca^{2+}$). Enhancing oil recovery in these strongly oil-wet and complex reservoirs presents several challenges. Conventional waterflooding techniques are ineffective in improving oil recovery under such conditions.

Chemical enhanced oil recovery (cEOR) is a highly promising technology that involves the injection of various chemicals, such as surfactants, polymers, alkali, smart water, nanoparticles, and more. These chemicals work to modify the interactional forces at the interfaces between the rock, oil, and brine, thereby enhancing oil productivity. cEOR can alter rock wettability, oil-water interfacial tension (IFT), and capillarity, enabling the displacement of untapped and residual oils towards the production well [Jarrahian et al., Colloids Surfaces A Physicochem. Eng. Asp. 410, 1-10, 2012; Sakthivel and Kanj, Energy Rep. 7, 4235-4248, 2021].

However, in many cases, conventional oilfield chemicals fail to withstand the harsh reservoir conditions, leading to insignificant impacts on wettability modification and IFT reduction, ultimately resulting in poor recovery. Moreover, factors such as pH, salinity, temperature, pressure, oil composition, rock type, mineralogy composition, and reservoir heterogeneity also influence wettability and oil recovery [Aghajanzadeh et al., J. Pet. Sci. Eng. 178, 700-710, 2019; Mohammed and Babadagli, Adv. Colloid Interface Sci. 220, 54-77, 2015].

Various types of nanoparticles, both inorganic (silicon oxide, titanium oxide, aluminum oxide, zirconium oxide, magnesium oxide, iron oxide) and organic (graphene particles, carbon nanotubes), have been investigated for their potential in wettability alteration and enhancing oil recovery in carbonate formations. These nanoparticles have been studied using methods such as imbibition or core flood experiments to evaluate their performance [Aghajanzadeh et al., J. Pet. Sci. Eng. 178, 700-710, 2019; Bayat et al., Energy Fuel, 28, 6255-6266, 2014].

US20220162498A1 discloses a method of enhancing oil recovery from a carbonate reservoir by placing into a subterranean formation a treatment fluid comprising a pore-connectivity enhancer comprising a phosphonoalkyl moiety, and a base fluid, wherein the base fluid includes sea water.

U.S. Ser. No. 10/836,952B2 discloses a method for enhancing oil recovery from a carbonate reservoir using an oil recovery formulation that includes carboxylic acid functionalized-pyrolyzed date leaf particles. The oil recovery formulation may also optionally include a cationic surfactant, wherein the cationic surfactant includes a protonated amine formed from a reaction between a $C_6$-$C_{26}$ alkyl amine compound and citric acid.

U.S. Ser. No. 11/555,143B2 discloses an oil and gas well servicing fluid comprising an aqueous base fluid, and a surfactant, wherein the aqueoud base fluid includes sea water and the surfactanct includes a protonated amine formed from a reaction between a $C_6$-$C_{26}$ alkyl amine compound and citric acid.

US20220162929A1 discloses a method of enhancing oil recovery comprising introducing into one or more injection wells located within a subterranean formation a treatment fluid comprising an aminopolycarboxylic acid comprising a phosphonoalkyl moiety, and a surfactant blend, and removing hydrocarbons from one or more production wells.

Boussa et al. [J. Can. Pet. Technol. 44, 16-21, 2005] discloses use of alkylamide aqueous solution to prevent precipitation of sodium chloride crystals from high chloride brines from the bottom of the hole to increase performance of a well.

Yang et al. [J. Pet. Sci. Eng. 212, 110204, 2022] discloses use of multi-alkylated aromatic amides amphiphiles containing benzene rings and a different number of alkyl side chains as asphaltene dispersants for Saudi crude oil to inhibit precipitation of asphaltenes in the crude oil tank.

The majority of oilfield chemicals employed for enhancing oil recovery are derived from oil-based starting materials through complex synthetic processes. This limits their scalability potential for field applications. Despite recent advancements in Enhanced Oil Recovery (EOR), there is a crucial need to enhance sustainability in the development of oilfield chemicals. This involves reducing $CO_2$ emissions and transitioning towards the use of eco-friendly materials to improve oil recovery in reservoirs with strong oil-wet characteristics and challenging reservoir conditions.

In view of the foregoing, it is one objective of the present disclosure to describe a method of enhancing oil recovery from a carbonate reservoir containing a hydrocarbon mixture. A second objective of the present disclosure is to describe a method of making a citric acid-based N-alkyl amides.

SUMMARY

In an exemplary embodiment, a method of enhancing oil recovery from a carbonate reservoir containing a hydrocarbon mixture is described. The method includes injecting the carbonate reservoir with a sea-water solution containing a citric acid-based additive having a formula (I) thereby forming a hydrocarbon mixture containing sea-water mixture; and separating the hydrocarbon mixture from the hydrocarbon mixture containing sea-water mixture to recover the hydrocarbon mixture. In some embodiments, $R_1$, and $R_2$ are each independently selected from the group consisting of an optionally substituted alkyl, an optionally substituted cycloalkyl, and an optionally substituted alkoxy, and wherein n is an integer from 2 to 8, to displace the hydrocarbon mixture from the carbonate reservoir. In some embodiments, the citric acid-based additive is present in the sea-water solution at a concentration of 1 to 1000 parts per million (ppm) based on a total number of parts by weight of the sea-water solution. In some embodiments, particles of the citric acid-based additive are adsorbed on surfaces of the carbonate rocks in the carbonate reservoir.

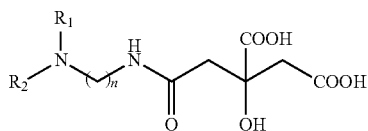

In a specific embodiment, the sea-water solution is an aqueous solution having a salinity of from 20,000 to 300,000 ppm based on the total number of parts by weight of the sea-water solution.

In another specific embodiment, the sea-water solution is natural sea water having a salinity of from 55,000 to 60,000 ppm based on the total number of parts by weight of the natural sea water.

In some embodiments, the $R_1$, and $R_2$ of formula (I) are each independently selected from the group consisting of methyl, ethyl, N-propyl, and isopropyl, and n is an integer from 2 to 4.

In a specific embodiment, the citric acid-based additive has a formula (II) or formula (III).

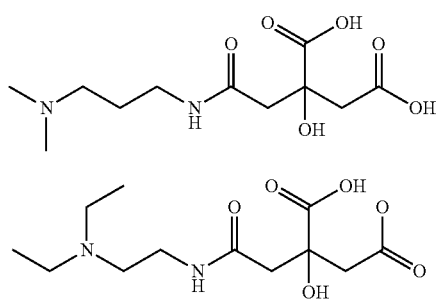

In some embodiments, the citric acid-based additive is present in the sea-water solution at a concentration of about 200 ppm based on the total number of parts by weight of the sea-water solution.

In some embodiments, a cumulative oil recovery of 40 to 50% based on a total amount of hydrocarbon recovered from the carbonate reservoir at about 100 degrees Celsius (° C.) and 3,000 pounds per square inch (psi).

In some embodiments, the carbonate reservoir has a temperature in a range of from 20 to 220° C., and a pressure in a range of 250 to 5,000 psi.

In some embodiments, a contact angle between a water droplet and a surface of hydrocarbon-wet carbonate rock in the carbonate reservoir is in a range of from 150 to 170 degrees (°) in the absence of the citric acid-based additive.

In some embodiments, after the injection, a contact angle between a water droplet and a surface of hydrocarbon-wet carbonate rock in the carbonate reservoir is in a range of from 100 to 120° in the presence of the citric acid-based additive.

In some embodiments, the hydrocarbon mixture contains at least one oil selected from the group consisting of crude oil, petroleum oil, shale oil, fossil oil, and biomass derived oil.

In some embodiments, the sea-water solution further contains at least one additive selected from the group consisting of an emulsifier, an anti-foaming agent, a fluid-loss additive, a viscosity modifier, a shale stabilizer, an alkali compound, a bridging agent, and a weighting agent.

In some embodiments, the emulsifier is selected from the group consisting of sodium lauryl sulfate (SLS), sodium dodecylbenzene sulfonate (SDBS), polyacrylate, tall oil fatty acid, and fatty amidoamine. In some embodiments, the anti-foaming agent is selected from the group consisting of polydimethylsiloxane, fatty acid ester, silicon dioxide, and vegetable oil. In some embodiments, the viscosity modifier is selected from the group consisting of a clay, a saccharide, a polysaccharide, a cellulose, an acrylate polymer and copolymer, and a polyvinyl polymer and copolymer. In some embodiments, the fluid-loss additive is selected from the group consisting of a starch, a starch derivative, a cellulose, and a cellulose derivative. In some embodiments, the shale stabilizer is selected from the group consisting of a sodium salt, and a sulfonated asphalt. In some embodiments, the alkali compound is selected from the group consisting of caustic soda and soda ash. In some embodiments, the bridging agent is selected from the group consisting of sodium borate, boric oxide, calcium carbonate, and magnesium oxide. In some embodiments, the weighting agent is selected from the group consisting of barite and hematite.

In some embodiments, the sea-water solution further contains at least one of an α-olefin sulfonate (AOS), and cetrimonium bromide (CTAB).

In some embodiments, the method further includes preparing the citric acid-based additive having the formula (I) by mixing citric acid, a diamine, and a fluoride salt to form a mixture, and heating the mixture thereby coupling an amine group of the diamine with a carboxylic acid group of the citric acid and drying to form the citric acid-based additive. In some embodiments, a molar ratio of the citric acid and the diamine is in a range of 1:2 to 2:1.

In some embodiments, the fluoride salt is present in the mixture at a concentration of 0.1 to 1 wt. % based on a total weight of the mixture.

In a specific embodiment, the fluoride salt contains at least one of calcium fluoride ($CaF_2$), sodium fluoride (NaF), and potassium fluoride (KF).

In some embodiments, the diamine has a formula (IV), wherein $R_1$, and $R_2$ are each independently selected from the group consisting of an optionally substituted alkyl, an optionally substituted cycloalkyl, and an optionally substituted alkoxy, and wherein n is an integer from 2 to 8.

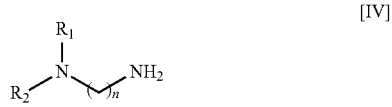

[IV]

In a specific embodiment, the diamine comprises at least one of N,N-dimethyl-1,3-propanediamine (DMPA), and N,N-diethylethylenediamine (DEEA).

In another specific embodiment, the heating is performed at a temperature of at least 150° C. for 4 to 96 hours.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
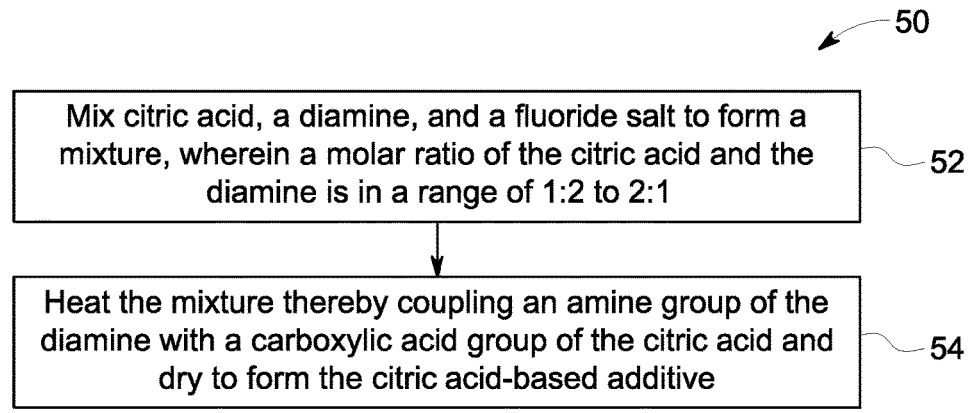
FIG. 1A illustrates a schematic flow chart of a method for preparing a citric acid-based additive having a formula (I), according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the term "enhanced oil recovery," "EOR" or "tertiary oil recovery" generally refers to a technique for increasing the amount of hydrocarbons that may be extracted from a "hydrocarbon-bearing formation" or "formation".

As used herein, the terms "hydrocarbon-bearing formation" or "formation" are generally used interchangeably and refer to a hydrocarbon-bearing formation in the field (i.e., subterranean hydrocarbon-bearing formations) and portions of such hydrocarbon-bearing formations (e.g., core samples)

As used herein, the term "reservoir" generally refers to a component of a petroleum system (i.e., hydrocarbon or petroleum-generating and storing geologic system) that is composed of a subsurface body of rock formations having sufficient porosity and permeability to store and transmit fluids.

As used herein, the term "carbonate reservoir" generally refers to a sedimentary rock reservoir having predominantly limestones. The reservoir may be, but is not limited to, a shale reservoir, a carbonate reservoir, a tight sandstone reservoir, a tight siltstone reservoir, a gas hydrate reservoir, a coalbed methane reservoir, etc.

As used herein the term "hydrocarbon mixture" generally refers to a combination of different hydrocarbons, i.e., to a combination of various types of molecules that contain carbon atoms and, in many cases, attached hydrogen atoms. The "hydrocarbon mixture" may comprise many different molecules having a wide range of molecular weights.

As used herein, the term "fluid loss additive" generally refers to a material capable of reducing volume of a filtrate that passes through a filter medium.

As used herein, the term "shale stabilizer" generally refers to a chemical substance that can be added to a treatment fluid to reduce shale sloughing.

As used herein, the term "bridging agent" generally refers to a material or substance that, when present in a treatment fluid, can bridge across the pore throat or fractures of an exposed rock, thereby building a filter cake to prevent or reduce loss of the treatment fluid or a portion thereof to a subterranean formation.

As used herein, the term "weighting agent" generally refers to particulates used to modulate the density of a treatment fluid.

As used herein, the term "olefin sulfonate" generally refers to a surfactant derived from direct sulfonation of olefin. The olefin from which the olefin sulfonate is derived is a mono-olefin having about 12 to 24 carbon atoms, preferably about 14 to 16 carbon atoms.

As used herein, the term "solution" generally refers to its normal meaning, as understood by one skilled in the art, e.g., a homogeneous mixture of a solid dissolved in a liquid. However, as used herein, the term "solution" is not intended to be read as necessarily requiring the absence of other, non-dissolved materials, or a that the solution is the continuous phase of a mixture.

As used herein, the term "aqueous solution" generally refers to a liquid having a relatively high polarity and being substantially immiscible with oils.

As used herein, the term "alkyl" unless otherwise specified, generally refers to both branched and straight-chain saturated aliphatic primary, secondary, and/or tertiary hydrocarbons of typically C1-C21.

As used herein, the term "cycloalkyl" generally refers to any univalent radical derived from a cycloalkane by removal of an atom of hydrogen having a C1-C10 carbon atoms.

As used herein, the term "alkoxy" generally refers to a group wherein the alkyl group is attached to an oxygen atom, and the "alkyl" part is the same as defined in the above-mentioned "alkyl".

As used herein, the term "substituted" refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—$NH_2$), alkylamino (-NHalkyl), cycloalkylamino (-NHcycloalkyl), arylamino (-NHaryl), arylalkylamino (-NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —$SO_2NH_2$), substituted sulfonamide (e.g., —$SO_2NH$alkyl, —$SO_2NH$aryl, —$SO_2NH$arylalkyl, or cases where there are two substituents on one nitrogen selected from alkyl, aryl, or alkylalkyl), nitro, cyano, carboxy, unsubstituted amide (i.e. —$CONH_2$), substituted amide (e.g., -CONHalkyl, -CONHaryl, -CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted and may be either unprotected or protected as necessary, as known to those skilled in the art.

As used herein, the term 'optionally substituted cycloalkyl' refers to the cycloalkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or heterocyclic (preferably heterocycloamino) optionally substituted with one or two groups independently selected from alkyl, hydroxyl, alkoxy, alkylsulfonyl, halo, or —CONRR' where R and R' are as defined above.

As used herein, the term 'optionally substituted alkyl' refers to the alkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or heterocyclic (preferably heterocycloamino) optionally substituted with one or two groups independently selected from alkyl, hydroxyl, alkoxy, alkylsulfonyl, halo, or —CONRR' where R and R' are as defined above.

Aspects of the present invention are directed to a method of enhancing oil recovery from a carbonate reservoir containing a hydrocarbon mixture using a citric acid-based additive, namely, citric acid-based N-alkyl amides. A sustainable synthesis of citric acid-based N-alkyl amides using solvent-free reaction and green starting material is also disclosed.

According to an aspect of the present disclosure, a method of enhancing oil recovery from a carbonate reservoir containing a hydrocarbon mixture is described. The carbonate reservoir may be selected or determined using well-established geologic sampling techniques. In some embodiments, the carbonate reservoir may comprise limestone, chalk, one or more clay minerals, quartz, feldspar, and one or more organic materials. In some further embodiments, the carbonate reservoir comprises carbonate rocks containing calcite ($CaCO_3$) and dolomite $CaMg(CO_3)_2$. The carbonate reservoir has a temperature in a range of 20 to 220° C., preferably 40 to 200° C., preferably 60 to 180° C., preferably 80 to 160° C., preferably 100 to 140° C., or even more preferably about 120° C., and a pressure in a range of 250 to 5,000 pounds per square inch (psi), preferably 500 to 4500 psi, preferably 1000 to 4000 psi, preferably 1500 to 3500 psi, preferably 2000 to 3000 psi, or even more preferably about 2500 psi.

A hydrocarbon mixture is displaced from the carbonate reservoirs thereby forming a hydrocarbon mixture containing sea-water mixture. The hydrocarbon mixture includes one or more oils selected from crude oil, petroleum oil, shale oil, fossil oil, and biomass-derived oil. To displace the hydrocarbon mixture from the carbonate reservoir, a sea-water solution including a citric acid-based additive is injected into the carbonate reservoir. The citric acid-based additive is present in the sea-water solution at a concentration of 1 to 1000 parts per million (ppm), preferably 100-900 ppm, preferably 200-800 ppm, preferably 200-600 ppm, preferably 200-500 ppm, based on a total number of parts by weight of the sea-water solution. In some embodiments, the sea-water solution is an aqueous solution having a salinity of from 20,000 to 300,000 ppm based on the total number of parts by weight of the sea-water solution, preferably 30,000 to 250,000 ppm, preferably 40,000 to 200,000 ppm, or 50,000 to 150,000 ppm. In some preferred embodiments, the sea-water solution is natural sea water having a salinity of from 55,000 to 60,000 ppm based on the total number of parts by weight of the natural sea water. The citric acid-based additive may be preferably mixed and dispersed in the sea water to form the sea-water solution. In some embodiments, the citric acid-based additive may be at least 90 wt. % dissolved in the sea-water by mass, preferably at least 95 wt. %, or even more preferably at least 99 wt. % dissolved in the sea-water by mass. Other ranges are also possible. The dissolved citric acid-based additive present in the sea-water solution may have a particles size of no more than 100 nm, preferably no more than 50 nm, preferably no more than 30 nm, preferably no more than 10 nm, or even more preferably no more 5 nm. In some embodiments, no more than 10 wt. % of the citric acid-based additive by mass present in the sea-water solution is in the form of oil-in-water emulsion, preferably no more than 5 wt. %, or even more preferably no more than 1 wt. % of the citric acid-based additive by mass present in the sea-water solution is in the form of oil-in-water emulsion. In some embodiments, the oil-in-water emulsion has a particle size in a range of 5 to 100 nm, preferably 8 to 80 nm, preferably 10 to 50, or even more preferably 13 to 30 nm. Other ranges are also possible. Upon injecting the sea-water solution containing the citric acid-based additive, the particles of the citric acid-based additive, in the form of a solute and/or an emulsion droplet, are adsorbed on the surfaces of the carbonate rocks in the carbonate reservoir. In some embodiments, the citric acid-based additive particles are adsorbed on surfaces and pores of the carbonate reservoir via at least one interaction selected from the group consisting of Van der Waals forces, electrostatic forces, hydrophobic interactions, chemical bonding, and steric hindrance. In some embodiments, one or more functional groups of the citric acid-based additive particles are chemically bonded to the calcium cations on surfaces and pores of the carbonate reservoir. In some embodiments, the one or more functional groups of the citric acid-based additive particles comprise one or more amine (—$NH_2$) groups, one or more alkyl chains (C1-C10), one or more carboxylate (COO—) groups, one or more hydroxyl (—OH) groups, one or more sulfonate (—$SO_3$—) groups, one or more phosphate (($PO_4$)$^{3-}$) groups, one or more ether (—O—) groups, one or more quaternary ammonium ($R_4N^+$) groups, one or more amide (—$CONH_2$) groups, and one or more epoxide (—O—) groups. In some preferred embodiments, the one or more functional groups comprise one or more quaternary ammonium ($R_4N^+$) groups, one or more hydroxyl (—OH) groups, one or more alkyl chains (C1-C10), and one or more carboxylate (COO—) groups.

In some embodiments, the citric acid-based additive is a compound of formula (I).

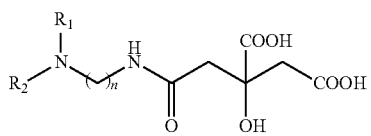

[I]

$R_1$, and $R_2$ are each independently selected from the group consisting of an optionally substituted alkyl, an optionally substituted cycloalkyl, and an optionally substituted alkoxy, and wherein n is an integer from 2 to 8. In some embodiments, $R_1$, and $R_2$ are each independently selected from the group consisting of methyl, ethyl, N-propyl, and isopropyl, and n is an integer from 2 to 4.

In a preferred embodiment, the citric acid-based additive has a formula (II) or formula (III).

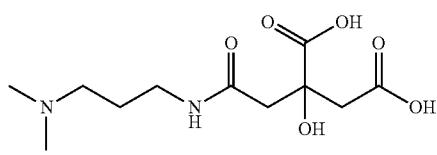

[II]

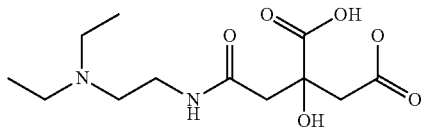

[III]

The sea-water solution may optionally include surfactants such as an α-olefin sulfonate (AOS), and/or cetrimonium bromide (CTAB). In some embodiments, the sea-water solution may further include at least one additive selected from the group consisting of an emulsifier, an anti-foaming agent, a fluid-loss additive, a viscosity modifier, a shale stabilizer, an alkali compound, a bridging agent, and a weighting agent. Typically, when present, the additive(s) may be incorporated in an amount of up to 5 wt. %, preferably up to 4 wt. %, preferably up to 3 wt. %, preferably up to 2 wt. %, preferably up to 1 wt. %, preferably up to 0.5 wt. %, preferably up to 0.1 wt. %, preferably up to 0.05 wt. %, preferably up to 0.01 wt. %, based on the total weight of the sea-water solution. Additive(s) suitable for use in oil and gas well operations, and particularly during oil recovery operations, are known by those of ordinary skill in the art.

A surfactant, when present in small amounts, reduces surface tension of a liquid, or increases its colloidal stability by inhibiting coalescence of bubbles. In some embodiments, the surfactants may be a nonionic surfactant, an anionic surfactant, a cationic surfactant, a viscoelastic surfactant, or a zwitterionic surfactant. In some embodiments, the surfactants may include, but are not limited to, ammonium lauryl sulfate, sodium lauryl sulfate (SLS), sodium dodecyl sulfate (SDS), alkyl-ether sulfates sodium laureth sulfate (sodium lauryl ether sulfate (SLES), sodium myreth sulfate, docusate (dioctyl sodium sulfosuccinate), perfluorooctanesulfonate (PFOS), perfluorobutanesulfonate, alkyl-aryl ether phosphates, alkyl ether phosphates, octenidine dihydrochloride; cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), CHAPS (3-[(3-cholamidopropyl)dimethylammonio]-1-propanesulfonate), cocamidopropyl hydroxysultaine, ocamidopropyl betaine, phospholipids, and sphingomyelins.

In some embodiments, the surfactant may include primary and secondary emulsifiers. Hereinafter, the primary and secondary emulsifiers are collectively referred to as the 'emulsifiers' or 'surfactants' and individually referred to as the 'emulsifier' or 'surfactant', unless otherwise specified. In some embodiments, the primary emulsifier is a polyaminated fatty acid. The primary emulsifier includes a lower hydrophilic-lyophilic balance (HLB) to the secondary emulsifier. In some embodiments, the primary emulsifier may include, but is not limited to, span 60, span 85, span 65, span 40, and span 20. In some embodiments, the primary emulsifier is sorbitan oleate, also referred to as the span 80. In some embodiments, the secondary emulsifier may include, but is not limited to, triton X-100, Tween 80, Tween 20, Tween 40, Tween 60, Tween 85, OP4, and OP 7. In some embodiments, the secondary emulsifier includes a biosurfactant such as a rhamnolipid surfactant.

Suitable examples of anti-foaming agents include, but are not limited to, silicone oils, silicone oil emulsions, organic defoamers, emulsions of organic defoamers, silicone-organic emulsions, silicone-glycol compounds, silicone/silica adducts, emulsions of silicone/silica adduct. Suitable examples of emulsifiers include, but are not limited to, a tallow amine, a ditallow amine, or combinations thereof, for example, a 50% concentration of a mixture of tallow alkyl amine acetates, C16-C18 (CAS-61790-60) and ditallow alkyl amine acetates (CAS 71011-03-5) in a suitable solvent such as heavy aromatic naphtha and ethylene glycol; as well as mixtures thereof.

The fluid loss additive controls loss of the citic acid-based additive when injected into the subterranean geological formation. The fluid loss additives may include, but is not limited to, starch, polysaccharides, silica flour, gas bubbles (energized fluid or foam), benzoic acid, soaps, resin particulates, relative permeability modifiers, degradable gel particulates, hydrocarbons dispersed in fluid, and one or more immiscible fluids. In some embodiments, the fluid loss additive may include the corn starch and poly(vinyl butyral)-co-vinyl alcohol-co-vinyl acetate (PVBA).

Suitable examples of the viscosity modifier or viscosifier include, but is not limited to sodium carbonate (soda ash), bauxite, dolomite, limestone, calcite, vaterite, aragonite, magnesite, taconite, gypsum, quartz, marble, hematite, limonite, magnetite, andesite, garnet, basalt, dacite, nesosilicates or orthosilicates, sorosilicates, cyclosilicates, inosilicates, phyllosilicates, tectosilicates, kaolins, montmorillonite, fullers earth, and halloysite. In some embodiments, the viscosifier may further include a natural polymer such as hydroxyethyl cellulose (HEC), carboxymethylcellulose, polyanionic cellulose (PAC), or a synthetic polymer such as poly(diallyl amine), diallyl ketone, diallyl amine, styryl sulfonate, vinyl lactam, laponite, polygorskites (such as attapulgite, sepiolite), and combinations thereof. In some embodiments, the viscosifier may further include one or more thickening agents such as XC-polymer, xanthan gum, guar gum, glycol, and combinations thereof. In some embodiments, the viscosifier is bentonite. The 'bentonite' may refer to potassium bentonite, sodium bentonite, calcium bentonite, aluminum bentonite, and combinations thereof, depending on the relative amounts of potassium, sodium, calcium, and aluminum in the bentonite. In some embodiments, the viscosifier is a corn starch.

The shale stabilizer is an additive of the sea-water solution that aids in the stabilization of shales and in controlling swelling clays. In some embodiments, the shale stabilizer is an alkali metal halide salt. Suitable examples include, but is not limited to, potassium chloride, sodium chloride, lithium chloride, rubidium chloride, and cesium chloride. In some embodiments, the shale stabilizer may include an alkaline earth metal halide salt. In some embodiments, the alkaline earth metal halide salt may include, but is not limited to, calcium chloride, and magnesium chloride.

The weighting agent is an agent that increases an overall density in order to provide sufficient bottom-hole pressure to prevent an unwanted influx of formation fluids. In some embodiments, the weighting agent may include, but is not limited to, calcium carbonate, barite, sodium sulfate, hematite, siderite, ilmenite. In some embodiments, the weighting agent is hydrophobic metallic zinc nanoparticles.

In some embodiments, an anti-scaling agent may be used. The anti-scaling agent inhibits the formation and precipitation of crystallized mineral salts that form scale. The anti-scaling agent may include, but is not limited to, phosphonates, acrylic co/ter-polymers, polyacrylic acid (PAA), phosphino poly carboxylic acid (PPCA), phosphate esters, hexamethylene diamine tetrakis (methylene phosphonic acid), diethylene triamine tetra (methylene phosphonic acid), diethylene triamine penta (methylene phosphonic acid) (DETA phosphonate), bis-hexamethylene triamine pentakis (methylene phosphonic acid) (BHMT phosphonate), 1-hydroxyethylidene 1,1-diphosphonate (HEDP phosphonate), and polymers of sulfonic acid on a polycarboxylic acid backbone. In some embodiments, the anti-scaling agent may further include phosphine, sodium hexametaphosphate, sodium tripolyphosphate and other inorganic polyphosphates, hydroxy ethylidene diphosphonic acid, butane-tricarboxylic acid, phosphonates, itaconic acid, and 3-allyloxy-2-hydroxy-propionic acid. In some embodiments, the sea-water solution may include metal sulfide scale removal agents such as hydrochloric acid.

In some embodiments, a corrosion inhibitor may be used. The corrosion inhibitor is a chemical compound that decreases the corrosion rate of a material, more preferably, a metal or an alloy, that comes into contact with the sea-water solution. The imidazoline can be, for example, derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline or an imidazoline derivative. Representative imidazoline derivatives include an imidazolinium compound or a bis-quaternized compound. In some embodiments, the corrosion inhibitor may include, but is not limited to, imidazolines, and amido amines. In some embodiments, the corrosion inhibitor may include, but is not limited to, oxides, sulfides, halides, nitrates, preferably halides, of metallic elements of group IIIa to VIa such as $SbBr_3$. The one or more additional corrosion inhibitors can be a phosphate ester, monomeric or polymeric fatty acid, alkoxylated amine, or mixture thereof.

The one or more corrosion inhibitor component can be a phosphate ester. Suitable mono-di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a C3-C18 aliphatic alcohol with phosphorous pentoxide. The phosphate intermediate interchanges its ester groups with triethylphosphate producing a broader distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include C6 to C10 alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred. The one or more corrosion inhibitors can be a monomeric or polymeric fatty acid. Preferred monomeric fatty acids are C14-C22 saturated and unsaturated fatty acids as well as polymeric products obtained by polymerizing one or more of such fatty acids. The one or more corrosion inhibitors can be an alkoxylated amine. The alkoxylated amine can be an ethoxylated alkyl amine. The alkoxylated amine can be ethoxylated tallow amine.

In some embodiments, a biocide may be used. The biocide is an additive of the sea-water solution that may kill microorganisms present in the drilling fluid composition. Biocides suitable for use may be oxidizing or non-oxidizing biocides. Oxidizing biocides can include, but are not limited to, bleach, chlorine, bromine, chlorine dioxide, peroxycarboxylic acid, peroxycarboxylic acid composition, and materials capable of releasing chlorine, bromine, or peroxide. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis (bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo [2.2.1]heptane-2,3-dicarboxylic acid, 4,5-dichloro-2-n-octyl-4-isothiazoline-3-one, 5-chloro-2-methyl-4-isothiazolin-3-one, and 2-methyl-4-isothiazolin-3-one.

Suitable non-oxidizing biocides also include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)).

Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxycarboxylic acid, peroxycarboxylic acid composition, and peroxides.

In an embodiment, the emulsifier one or more of SLS, SDBS, polyacrylate, tall oil fatty acid, and fatty amidoamine; the anti-foaming agent is one or more of polydimethylsiloxane, fatty acid ester, silicon dioxide, and vegetable oil; the viscosity modifier is one or more of a clay, a saccharide, a polysaccharide, a cellulose, an acrylate polymer and copolymer, and a polyvinyl polymer and copolymer; the fluid-loss additive is one or more of a starch, a starch derivative, a cellulose, and a cellulose derivative; the shale stabilizer is one or more of a sodium salt, and a sulfonated asphalt; the alkali compound is one or more of caustic soda and soda ash; the bridging agent is one or more of sodium borate, boric oxide, calcium carbonate, and magnesium oxide; and the weighting agent is one or more of barite and hematite.

In some embodiments, the sea water solution is substantially free of an additive (emulsifier, an anti-foaming agent, a fluid-loss additive, a viscosity modifier, a shale stabilizer, an alkali compound, a bridging agent, and a weighting agent).

The methods of the present disclosure generally relate to the recovery of hydrocarbons from a reservoir involving injection of the sea water solution including the citric acid-based additive into the reservoir to aid/enhance the recovery of hydrocarbons from the reservoir. The method can be used in secondary recovery processes such as water-flooding or surfactant flooding processes, or in tertiary recovery processes such as enhanced oil recovery (e.g., chemical injection EOR).

Chemical EOR is an oil recovery enhancement method that is designed to alter the original properties of oil. While typically carried out after secondary recovery, the techniques employed during enhanced oil recovery can be initiated at any time during the productive life of an oil reservoir. The purpose of EOR is to restore formation pressure and improve oil displacement or fluid flow in the reservoir.

The sea water solution, including the citric acid-based additive, and any optional additives may be added using any addition/dosing/mixing techniques known by those of ordinary skill in the art, including both manual and automatic addition techniques. For example, the addition may be carried out by using inline static mixers, inline mixers with velocity gradient control, inline mechanical mixers with variable speed impellers, inline jet mixers, motorized mixers, batch equipment, and appropriate chemical injection pumps and/or metering systems.

In any of the above applications, the sea-water solution, including the citric acid-based additive, may be injected down a well bored into a hydrocarbon-bearing geological formation. The method may be performed by injecting the sea-water solution, including the citric acid-based additive, into a first wellbore (e.g., an injection wellbore) connected to the reservoir and then collecting hydrocarbons containing sea-water solution from a second wellbore (e.g., a production wellbore) that is connected to the reservoir. Alternatively, the method may be performed by injecting the sea water solution, including the citric acid-based additive, into a wellbore connected to the reservoir and then collecting hydrocarbons from the same wellbore. The injection may proceed through suitable injection lines to areas where additional oil recovery (i.e., after primary recovery) is desired through capillaries or umbilical lines. The injection may be performed manually, or it may be automatic, for example, by using a chemical injection pump. In any of the above applications, the sea-water solution, including the citric acid-based additive, or any of its components combinable downhole may be injected continuously and/or in batches. The chemical injection pump(s) can be automatically or manually controlled to inject any amount of the sea water solution, including the citric acid-based additive, needed for secondary and/or tertiary oil recovery operations.

Injection pressures and temperatures of the sea-water solution may be kept constant or varied. In some embodiments, the injection pressure of the sea-water solution, including the citric acid-based additive, is up to 6,000 psi, preferably 25 to 6,000 psi, preferably 50 to 6,000 psi, preferably 100 to 5,750 psi, preferably 250 to 5500 psi. Other ranges are also possible.

The sea-water solution, including the citric acid-based additive, used herein may substantially increase the yield of hydrocarbons from underground reservoirs such as carbonate reservoirs (e.g., predominantly limestone) or sandstone reservoirs (e.g., primarily siliclastic rocks and clay), and may be particularly useful for increasing the yield of hydrocarbons in reservoirs of high-temperature water sources, high salinity water sources, or high temperature/high salinity water sources, for example, from carbonate reservoirs. Alternatively, the reservoir may be a tight shale reservoir formed by hydraulic fracturing. In some embodiments, the reservoir has a temperature of 10 to 450° C., preferably 20 to 400° C., and more preferably 20 to 300° C., and yet more preferably 20-220° C. Other ranges are also possible.

The hydrocarbon displaced from the reservoir, and subsequently collected, is preferably a crude oil. The crude oil may be a very light crude oil such as Arab Extra Light, Arab Super Light, or Arab Super Light Ardjuna crude oil (e.g., a jet fuel, gasoline, kerosene, petroleum ether, petroleum spirit, or petroleum naphtha crude oil), a light crude oil such as Arab Light or Arab Light/Seg 17 Blend crude oil (e.g., grade 1 and grade 2 fuel oil, diesel fuel oil, domestic fuel oil), a medium crude oil such as Arab Medium crude oil, and a heavy crude oil such as Arab Heavy crude oil (e.g., grade 3, 4, 5, and 6 fuel oil, heavy marine fuel). Both sweet (sulfur volume lower than 0.50%) and sour (sulfur volume higher than 0.50%) crude oils may be displaced and recovered/collected according to the methods herein.

In preferred embodiments, the crude oil is a light or medium crude oil, preferably a light crude oil, preferably Arabian Light crude oil, preferably Arabian Light crude oil having a density at 25° C. of 0.81 to 0.83 g/mL, preferably 0.815 to 0.8298 g/mL, preferably 0.82 to 0.8296 g/mL, preferably 0.822 to 0.8294 g/mL, preferably 0.824 to 0.829 g/mL, preferably 0.826 to 0.8288 g/mL, preferably 0.828 to 0.8286 g/mL.

Figure 5A:
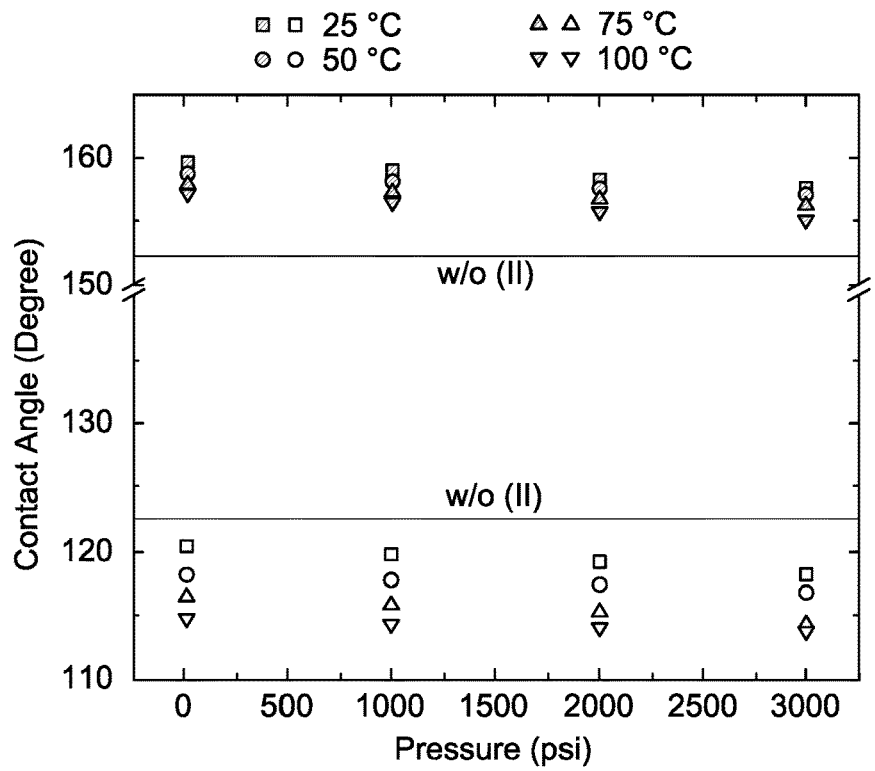
FIG. 5A shows a plot displaying effect of the citric acid-based additives of formula (II) on contact angle between water droplet and surface of hydrocarbon-wet carbonate rock sample as a function of temperature and pressure, according to certain embodiments.
Figure 5B:
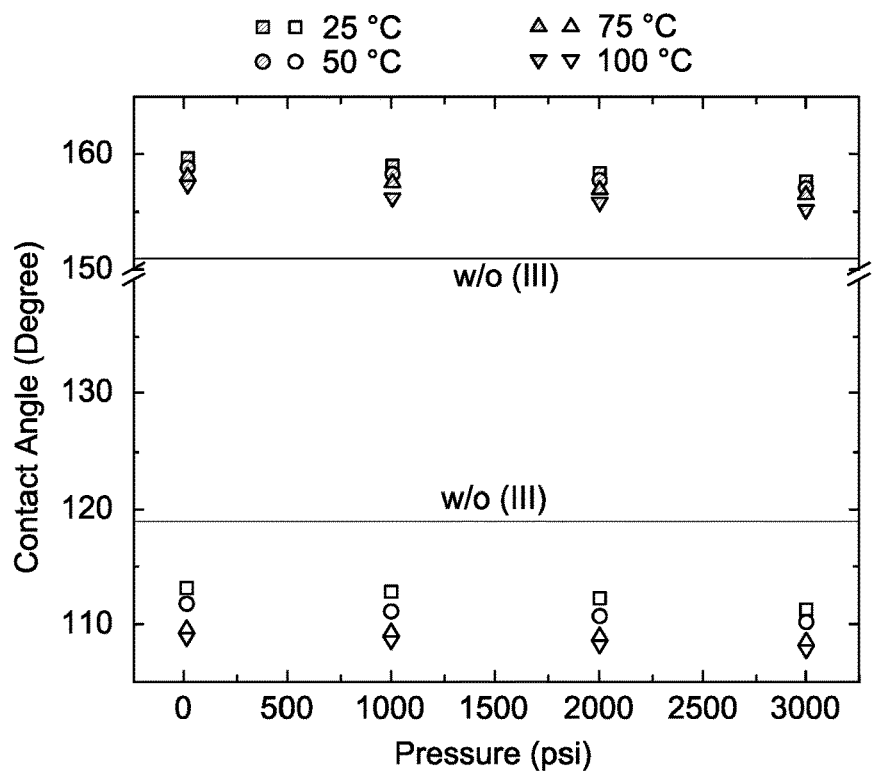
FIG. 5B shows a plot displaying effect of the citric acid-based additives of formula (III) on contact angle between water droplet and surface of hydrocarbon-wet carbonate rock sample as a function of temperature and pressure, according to certain embodiments.
Figure 6:
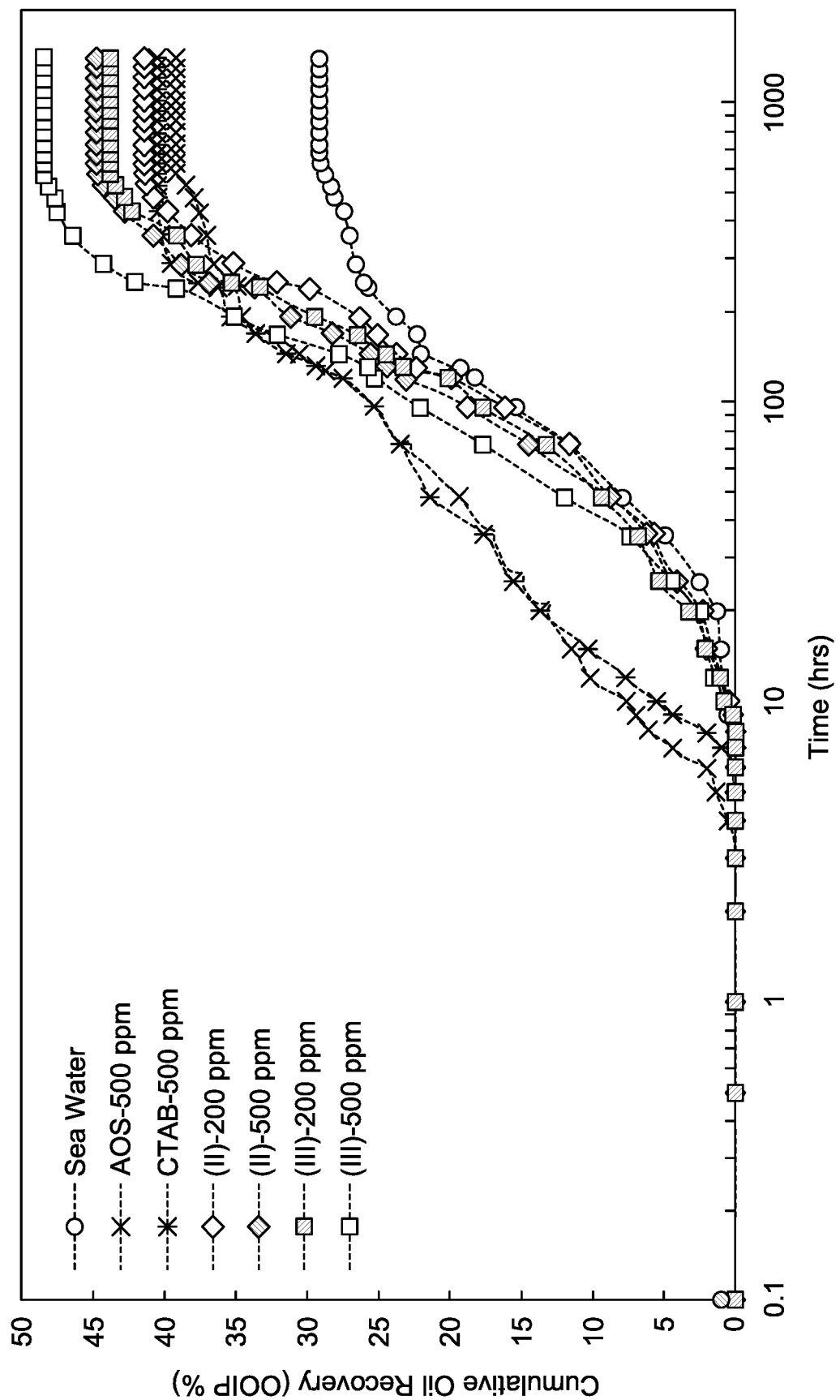
FIG. 6 shows a plot displaying effect of known surfactants and the citric acid-based additives of formula (II) and (III) on cumulative oil recovery as a function of time, according to certain embodiments.

As used herein, the term "contact angle," or "water contact angle" generally refers to the angle formed at the interface between a liquid droplet and a solid surface. It is the angle measured between the solid surface and the tangent line drawn at the point where the liquid droplet meets the solid surface. In the present disclosure, the contact angle between a water droplet and a surface of hydrocarbon-wet carbonate rock in the carbonate reservoir is in a range of from 150 to 170 degrees (°) in the absence of the citric acid-based additive, as depicted in FIGS. 5A and 5B. However, after the injecting, a contact angle between a water droplet and a surface of hydrocarbon-wet carbonate rock in the carbonate reservoir is in a range of from 100 to 120° in the presence of the citric acid-based additive, preferably 105 to 115°, or even more preferably about 110°, as depicted in FIGS. 5A and 5B. Upon injection of the citric acid-based additive, the cumulative oil recovery of 40 to 50% based on a total amount of hydrocarbon recovered from the carbonate reservoir at about 100 degrees Celsius (° C.) and 3,000 pounds per square inch (psi), as depicted in FIG. 6.

After the injecting, the hydrocarbon (e.g., crude oil)/seawater mixture brought to the surface may then be separated using techniques known to those of ordinary skill in the art into respective aqueous and oil phases for further processing (e.g., crude oil refining/upgrading/processing). For example, the oil/water mixture may be separated at a fluids processing facility using emulsion breakers, water clarifiers, and/or other oil/water separation techniques known to those of ordinary skill in the art, such as by using gravity oil separators (API separators), plate separators or coalescing plate separators, separatory funnels, settling tanks, centrifugal separation (e.g., centrifugal water-oil separators, centrifugal settling devices, dewatering centrifuges), decanters, induced gas floatation such using microbubble technology, and skimming equipment.

FIG. 1 illustrates a schematic flow chart of a method 50 for preparing a citric acid-based additive having a formula (I). The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes mixing citric acid, a diamine, and a fluoride salt to form a mixture. In some embodiments, a molar ratio of the citric acid and the diamine is in a range of 1:2 to 2:1, preferably 1:1.5 to 1.5:1, or even more preferably about 1:1. In some embodiments, the fluoride salt is present in the mixture at a concentration of 0.1 to 1 wt. % based on a total weight of the mixture, preferably 0.2 to 0.8 wt. %, preferably 0.3 to 0.6 wt. %, or even more preferably about 0.5 wt. %. Other ranges are also possible. Suitable examples of the fluoride salt include at least one of calcium fluoride ($CaF_2$), sodium fluoride (NaF), and potassium fluoride (KF). The diamine is a compound of Formula (IV)

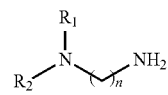

[IV]

wherein $R_1$, and $R_2$ are each independently selected from the group consisting of an optionally substituted alkyl, an optionally substituted cycloalkyl, and an optionally substituted alkoxy, and wherein n is an integer from 2 to 8. In an embodiment, the diamine comprises at least one of N,N-dimethyl-1,3-propanediamine (DMPA), and N,N-diethyl-ethylenediamine (DEEA).

At step 54, the method 50 includes heating the mixture thereby coupling an amine group of the diamine with a carboxylic acid group of the citric acid and drying to form the citric acid-based additive. In an embodiment, the heating is performed at a temperature of at least 150° C., preferably 150-200° C., preferably 160-200° C., preferably 160° C. for 1-3 hours, preferably 1 hour. The heated mixture is further dried for 4 to 96 hours, preferably 10-72 hours, preferably 20-50 hours, preferably 30-48 hours, and preferably 48 hours, to obtain the citric acid-based additive. The drying can be done by using heating appliances such as ovens, microwaves, autoclaves, hot plates, heating mantles and tapes, oil baths, salt baths, sand baths, air baths, hot-tube furnaces, and hot-air guns. In a preferred embodiment, the drying is performed under vacuum to prevent oxidation.

Figure 2:
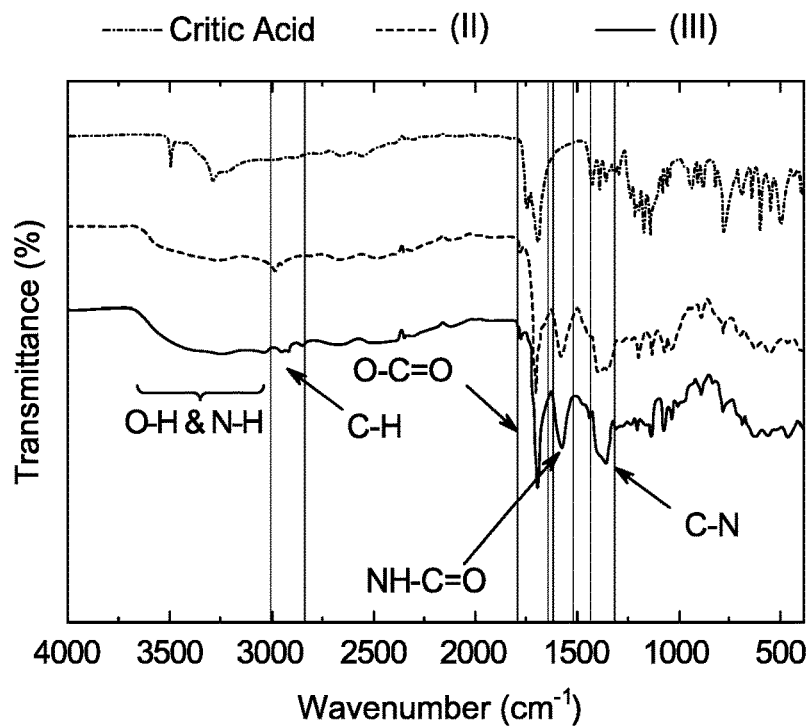
FIG. 2 shows an overlay of Fourier Transform Infrared (FTIR) spectra of citric acid and the citric acid-based additives of formula (II) and formula (III), according to certain embodiments.

The structures of the citric acid-based additive may be characterized by Fourier transforms infrared spectroscopy (FT-IR). In some embodiments, the FT-IR may be collected in a Nicolet 6700 Thermo Scientific instrument acquired in a range of 4000 to 400 centimeter inverse (cm−1) at 4 cm−1 resolution. 20 scans were carried out for each sample. In some embodiments, the citric acid-based additive has peaks at 800 to 1050 $cm^{-1}$, 1100 to 1700 $cm^{-1}$, and 3000 to 3500 $cm^{-1}$ in a Fourier transform infrared spectrum (FT-IR), as depicted in FIG. 2. Other ranges are also possible.

The thermostability of the citric acid-based additive was characterized by thermal gravimetric analysis (TGA). TGA analysis is performed by using a thermogravimetric analyzer (SDT Q 600, TA Instruments, New Castle, USA). For the TGA analysis, the samples are measured by heating at an increment frequency of 5 to 20° C./min with the flow of nitrogen in a range of 25 to 150 mL/min, and a temperature of up to 1200° C. Other ranges are also possible.

Figure 3:
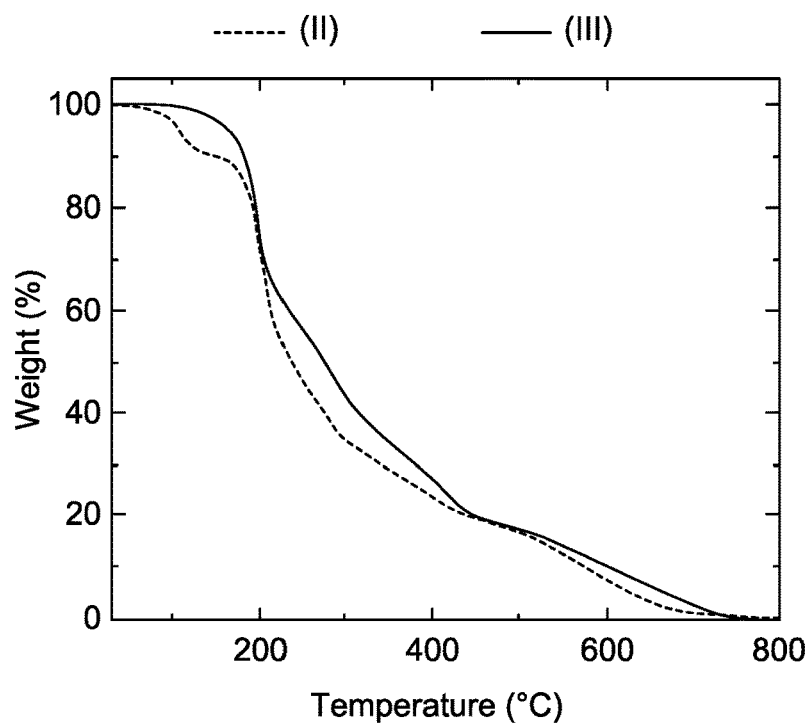
FIG. 3 shows an overlay of thermogravimetric analysis (TGA) curve of the citric acid-based additives of formula (II) and formula (III), according to certain embodiments.

Referring to FIG. 3 a thermogravimetric analyzer (TGA) curve of the citric acid-based additive, in some embodiments, the citric acid-based additive has a mass loss of up to 20 wt. % based on an initial weight of the citric acid-based additive at a temperature of less than or equal to 200° C., as depicted in FIG. 3. In some further embodiments, the citric acid-based additive has a mass loss of up to 80 wt. % based on an initial weight of the citric acid-based additive at a temperature of less than or equal to 500° C., as depicted in FIG. 3.

Figure 4:
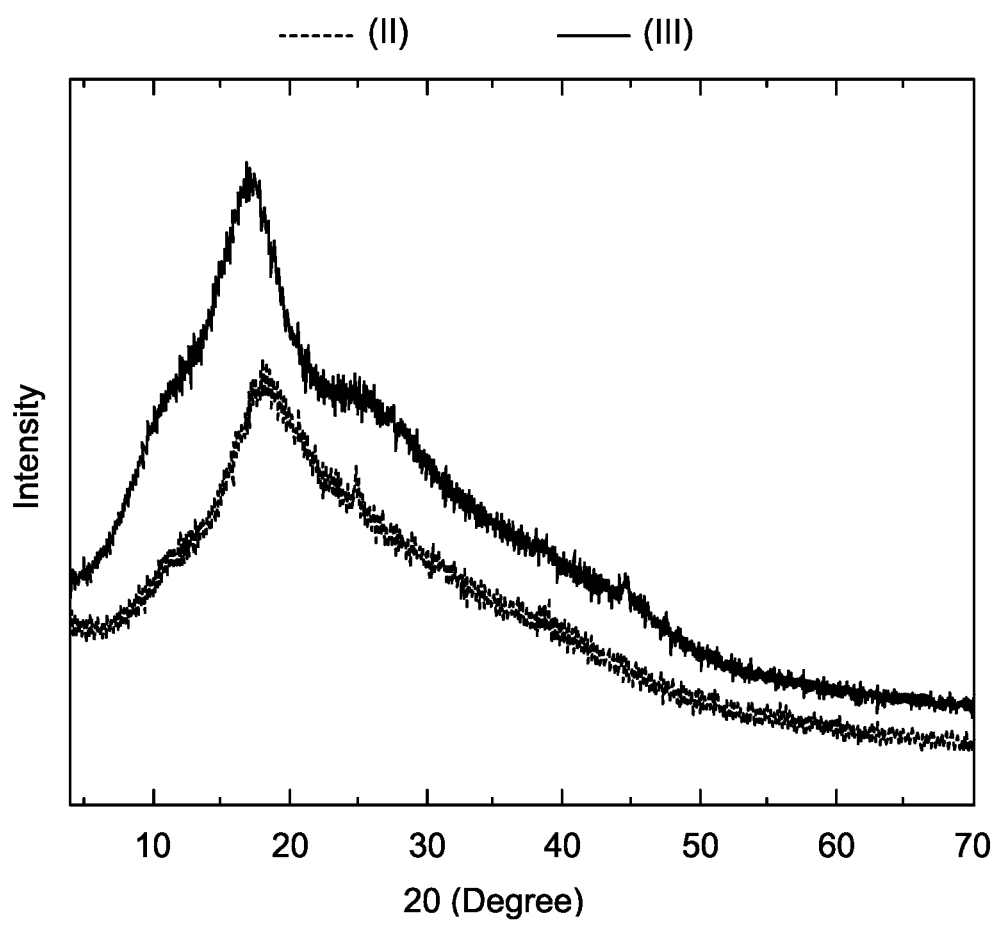
FIG. 4 shows an overlay of wide-angle X-ray diffraction (XRD) spectra of the citric acid-based additives of formula (II) and formula (III), according to certain embodiments.

The crystalline structures of the citric acid-based additive may be characterized by X-ray diffraction (XRD). In some embodiments, the XRD may be a wide-angle XRD. The XRD patterns are collected in a Rigaku MiniFlex diffractometer equipped with a Cu-Kα radiation source (λ=0.15406 nm) for a 2θ range extending between 5 and 80°, preferably 15 and 70°, further preferably 30 and 60° at an angular rate of 0.005 to 0.04° s$^{-1}$, preferably 0.01 to 0.03° s$^{-1}$, or even preferably 0.02° s$^{-1}$. In some embodiments, the citric acid-based additive has at least a first intense peak with a 2 theta (θ) value in a range of 10 to 30°, preferably about 20, as depicted in FIG. 4. Other ranges are also possible.

$^1$H and $^{13}$C NMR spectra may be recorded on a 400 MHz spectrometer (Bruker AvanceIII) using the residual DMSO-d$_6$ at δ 2.50 ppm and $^{13}$C DMSO-d$_6$ signal at δ 39.52 ppm as internal standards.

Figure 9:
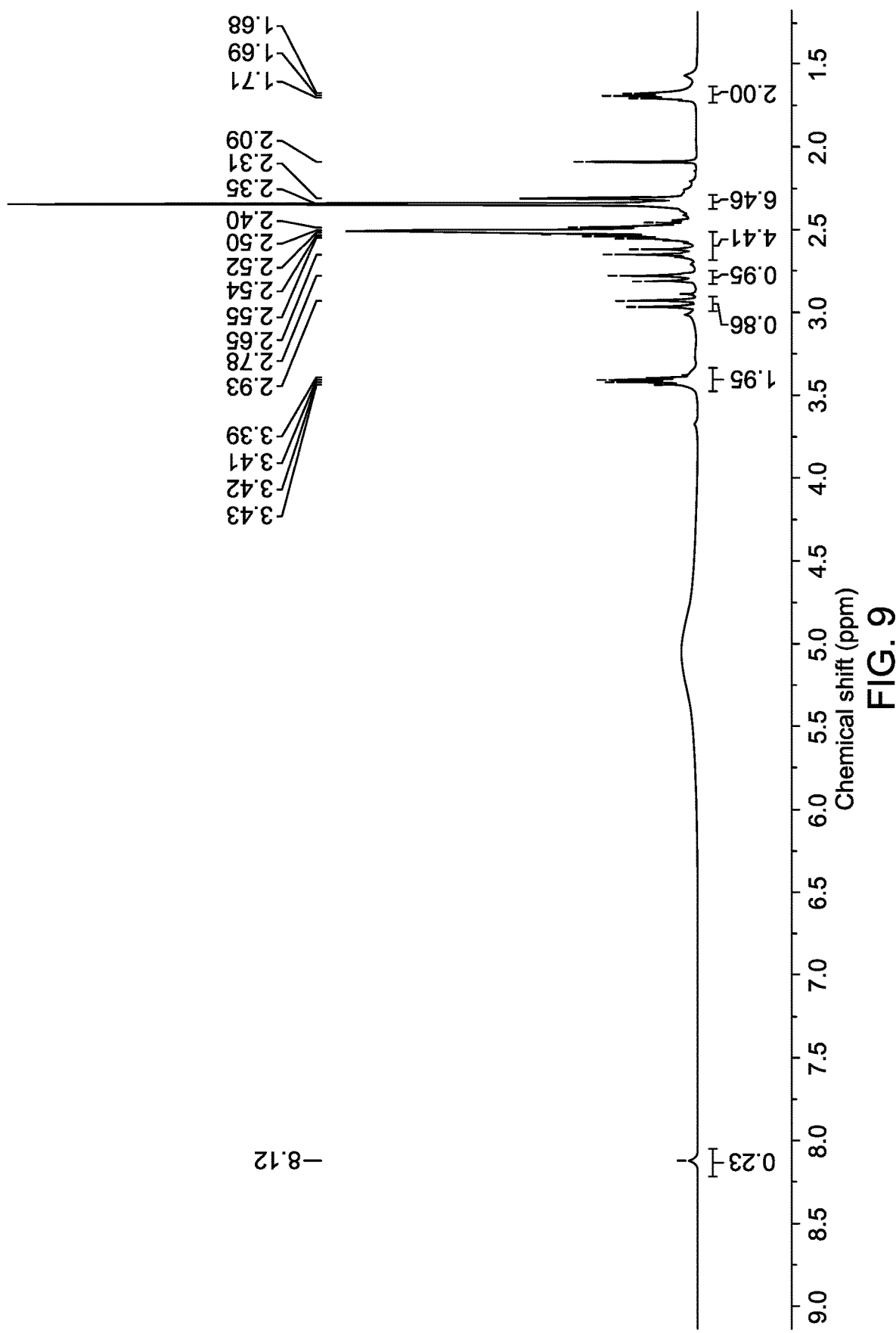
FIG. 9 depicts a $^1$H NMR spectra of CA-DMPA in DMSO-$d_6$, according to certain embodiments.

Referring to FIG. 9, $^1$H nuclear magnetic resonance (NMR) spectra of the citric acid-based additive of formula [II] in DMSO-d$_6$. In some embodiments, the citric acid-based additive of formula [II] has a first peak in a range of 1.5 to 1.9, or more preferably about 1.69; a second peak in a range of 2.3 to 2.5, or more preferably about 2.4; a third peak in a range of 2.5 to 2.6, or more preferably about 2.5 to 2.55; a fourth peak in a range of 2.6 to 3.1, or more preferably about 2.65 to 2.93; a fifth peak in a range of 3.2 to 3.6, or even more preferably about 3.39 to 3.43; a sixth peak in a range of 8 to 8.3, or more preferably about 8.12, as depicted in FIG. 9. Other ranges are also possible.

Figure 10:
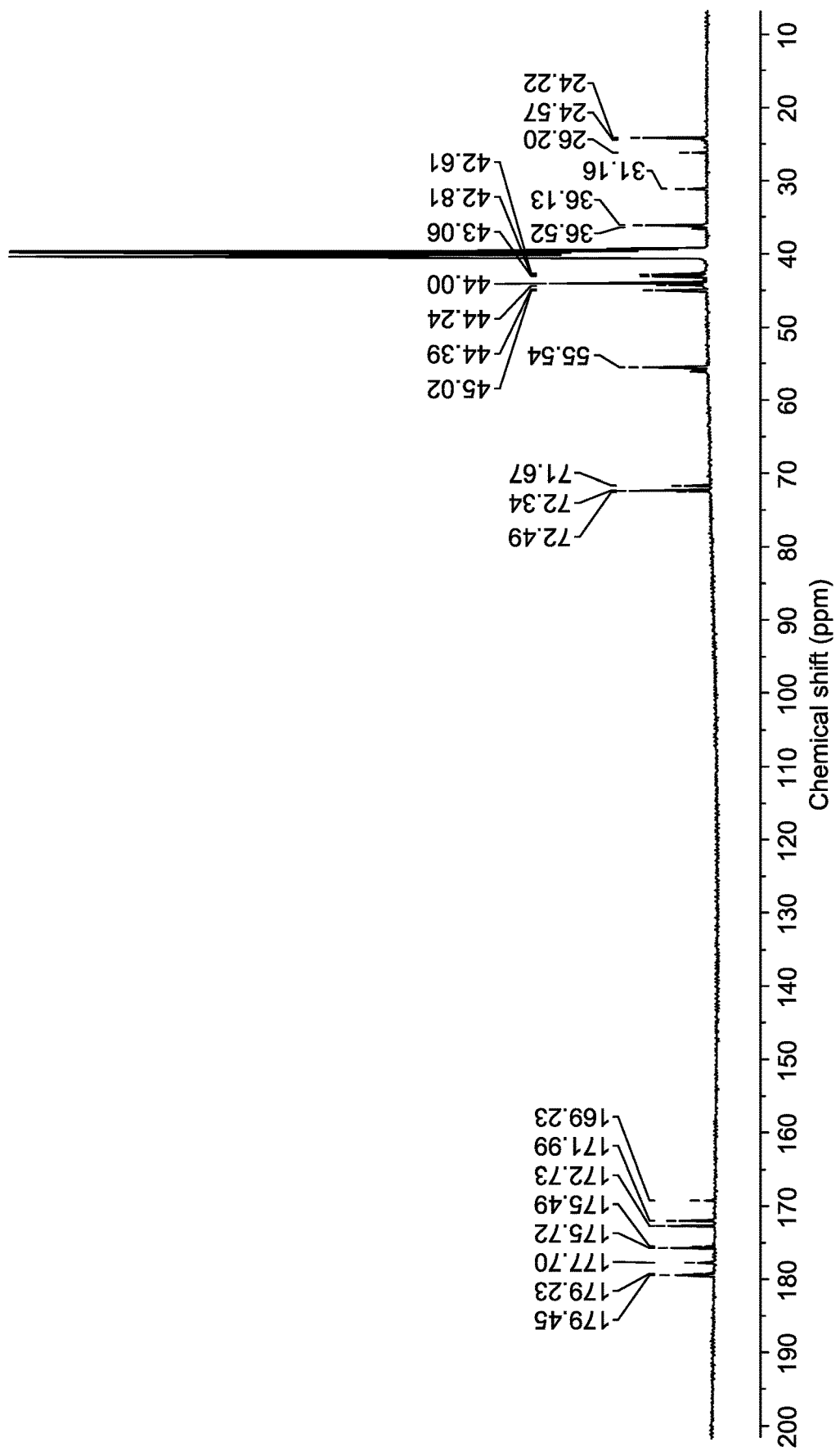
FIG. 10 depicts a $^{13}$C NMR spectra of CA-DMPA in DMSO-$d_6$, according to certain embodiments.
Figure 11:
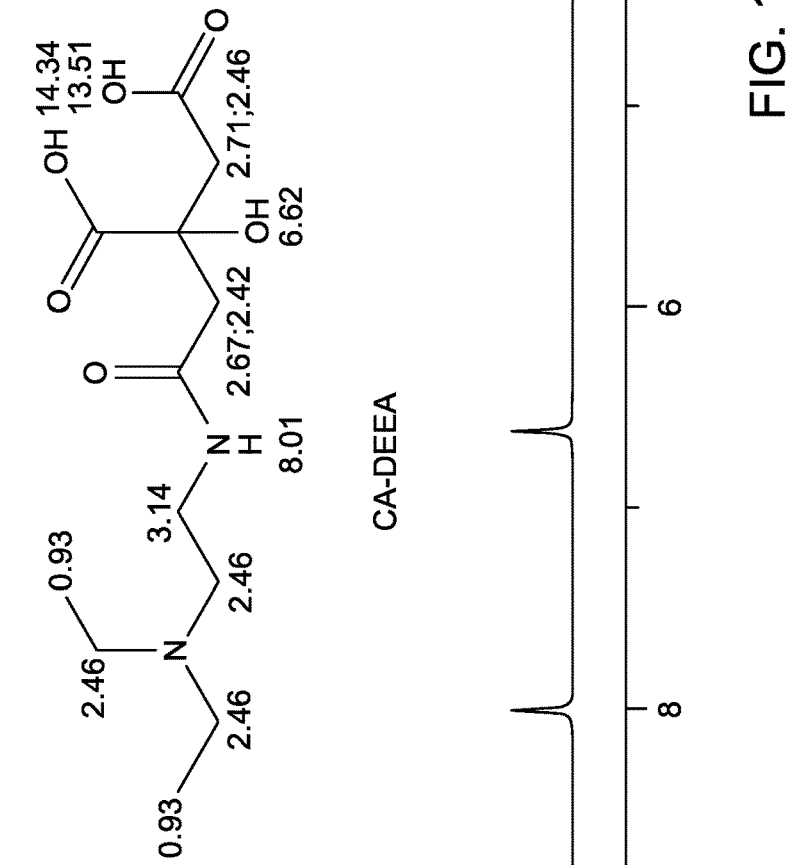
FIG. 11 depicts a predicted $^1$H nuclear magnetic resonance (NMR) spectra of 2-(2-((2-(diethylamino)ethyl)amino)-2-oxoethyl)-2-hydroxysuccinic acid (CA-DEEA), according to certain embodiments.

Referring to FIG. 10, $^{13}$C NMR spectra of the citric acid-based additive of formula [II] in DMSO-d$_6$. In some embodiments, the citric acid-based additive of formula [II] has peaks in a range of 10 to 190, or more preferably about 24.2, 24.6, 26.2, 31.2, 36.1, 43, 44, 44.4, 45, 55.54, 71.2, 72.3, 169.2, 172, 172.7, 175.7, 177.7, 179.2, 179.45, as depicted in FIG. 10. Other ranges are also possible.

Figure 12:
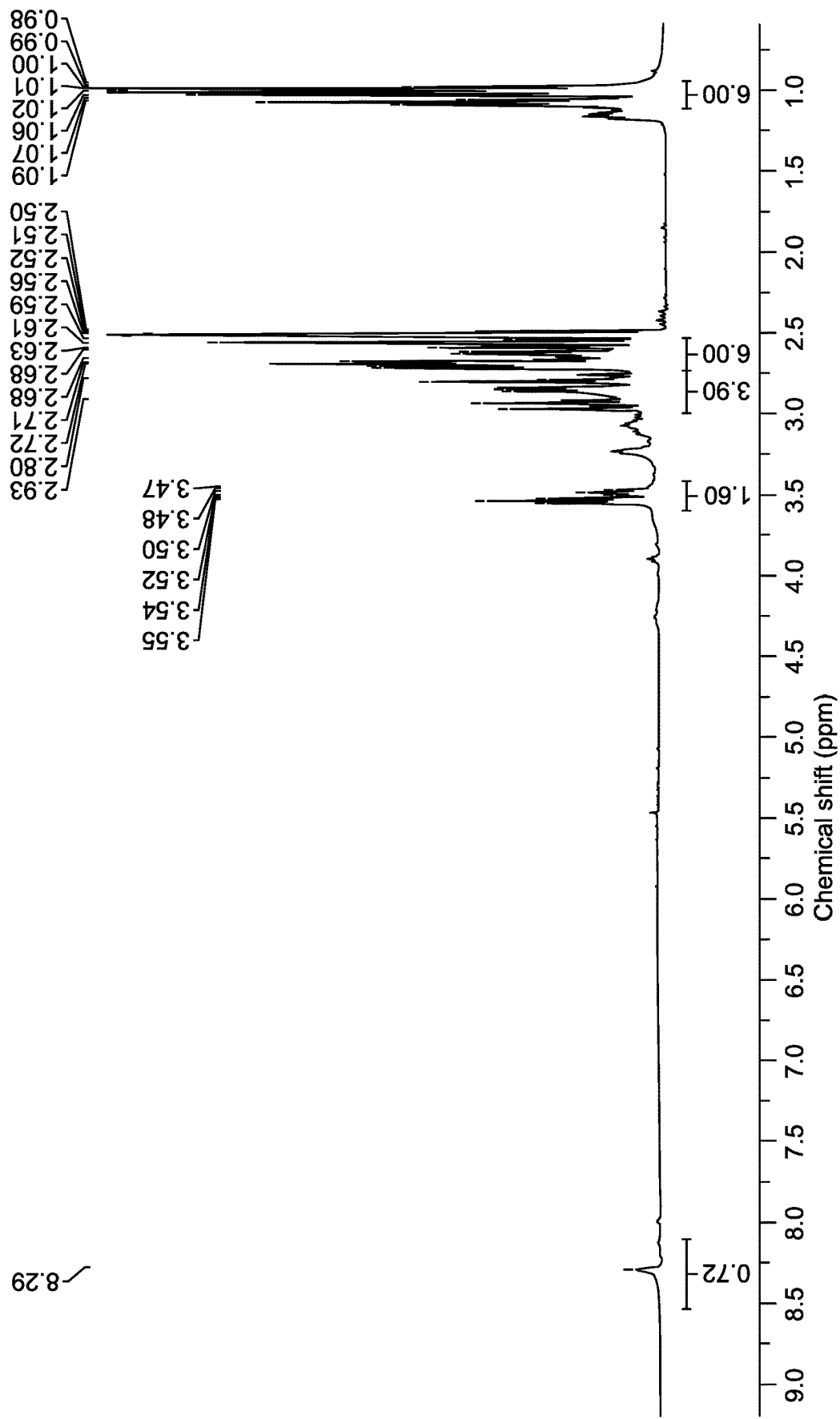
FIG. 12 depicts a $^1$H NMR spectra of CA-DEEA in DMSO-$d_6$, according to certain embodiments.

Referring to FIG. 12, $^1$H nuclear magnetic resonance (NMR) spectra of the citric acid-based additive of formula [III] in DMSO-d$_6$. In some embodiments, the citric acid-based additive of formula [III] has a first peak in a range of 1 to 1.2, or more preferably about 1.0 to 1.07; a second peak in a range of 2.5 to 2.7, or more preferably about 2.6 to 2.71; a third peak in a range of 2.7 to 3.0, or more preferably about 2.72 to 2.93; a fourth peak in a range of 3.3 to 3.8, or more preferably about 3.47 to 3.55; a fifth peak in a range of 8 to 8.5, or even more preferably about 8.29, as depicted in FIG. 12. Other ranges are also possible.

Figure 13:
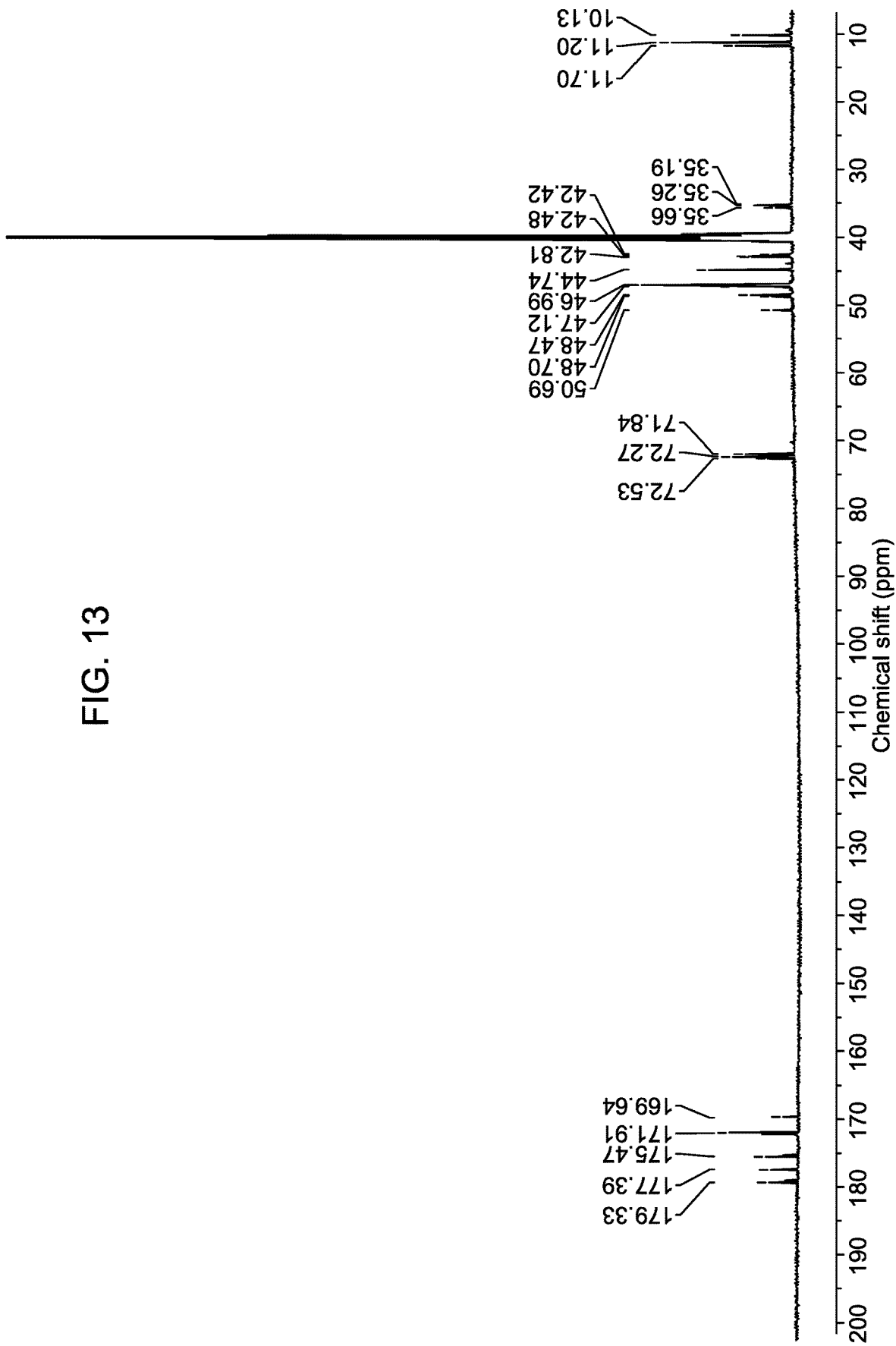
FIG. 13 depicts a $^{13}$C NMR spectra of CA-DEEA in DMSO-$d_6$, according to certain embodiments.

Referring to FIG. 13, $^{13}$C NMR spectra of the citric acid-based additive of formula [III] in DMSO-d$_6$. In some embodiments, the citric acid-based additive of formula [III] has peaks in a range of 10 to 190, or more preferably about 10.1, 11.2, 11.7, 35.2, 35.6, 42.5, 42.7, 42.8, 44.7, 47, 47.1, 48.7, 50.7, 71.8, 72.3, 72.5, 169.6, 171.9, 175.5, 177.4, 179.3, as depicted in FIG. 13. Other ranges are also possible.

The resulting N-alkyl amide compounds demonstrated good stability in reservoir conditions and were used for enhanced oil recovery. In some embodiments, the citric acid-based N-alkyl amides resulted in cumulative oil recovery of 44.7%-48.3%, which is 90% higher than the commonly used surfactants such as an α-olefin sulfonate (AOS) and cetrimonium bromide (CTAB).

EXAMPLES

The following examples demonstrate a method of making enhancing oil recovery from a carbonate reservoir containing a hydrocarbon mixture is described. The examples are provided solely for illustration and are not to be construed as limitations of the present disclosure, as many variations thereof are possible without departing from the spirit and scope of the present disclosure.

Example 1: Materials

Citric acid-based additives having formula (II) or (III) were prepared by melt condensation at a high temperature and without using any solvent. A scheme for the synthesis of citric acid-based additives of formula (II) and formula (III) is shown in FIG. 1B.

Example 2: Synthesis of Citric Acid-Based Additive of Formula (II)

Figure 1B:
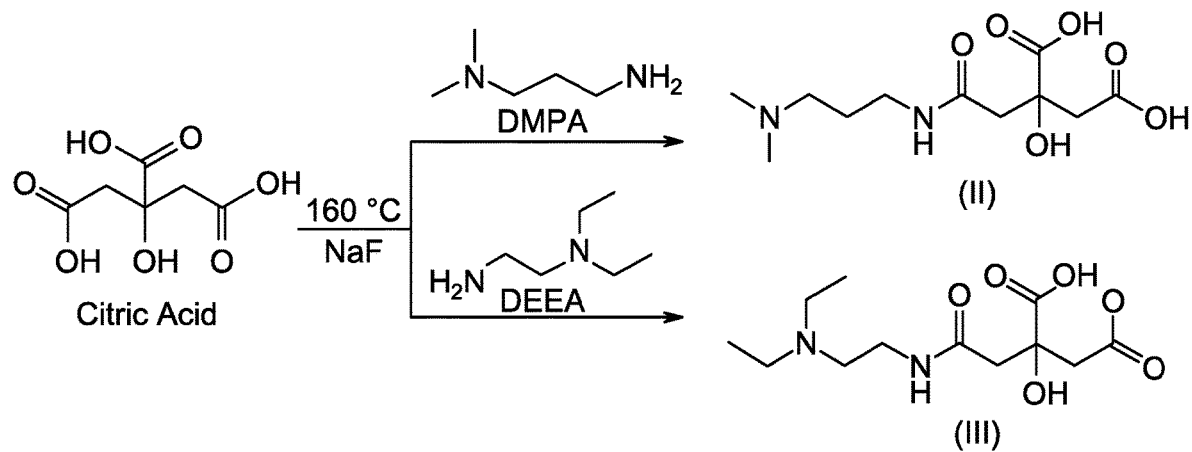
FIG. 1B shows a scheme for making citric acid-based additives of formula (II) and formula (III), according to certain embodiments.

Referring to FIG. 1B, the citric acid (10 g, 52 mmol) and dimethylolpropionic acid (DMPA) (5.32 g, 52 mmol) were placed in two neck round-bottom flasks equipped with an air condenser. NaF (0.11 g, 2.6 mmol) was added to the reaction medium. The reaction was kept under stirring at 160° C. for one hour. The obtained orange sticky solid was collected and dried under vacuum for 48 h (10.4 g, 67.8% yield). The obtained product was used as is without any further purification. The chemical structure of the compound of formula (II) was confirmed by $^1$H and $^{13}$C NMR and Fourier transform infrared (FTIR).

$^1$H NMR (400 MHz, DMSO-d$_6$, δ): 1.69 (m, 2H), 2.4 (s, 6H), 2.5-2.55 (m, 4H), 2.65-2.93 (m, 2H), 3.39-3.43 (m, 2H), 8.12 (br s, NH). $^{13}$C NMR (100 MHz, DMSO-d$_6$, δ): 24.2, 24.6, 26.2, 31.2, 36.1, 43, 44, 44.4, 45, 55.54, 71.2, 72.3, 169.2, 172, 172.7, 175.7, 177.7, 179.2, 179.45.

Referring now to FIG. 2, the FTIR spectrum of the compound of formula (II), the —OH and —NH adsorption bands were found between 3000 and 3700 cm$^{-1}$, while the C=O asymmetric stretching (O—C=O asym, str) and symmetric stretching (O—C=O sym, str) bands of carboxylic acid groups were located at 1780 and 1702 cm$^{-1}$, respectively. Moreover, the C=O stretching of the amide group (NH—C=O, str) was found at 1577 cm$^{-1}$. Also, the C—N stretching (C—N, str) was found at 1392 cm$^{-1}$.

Example 3: Synthesis of Citric Acid-Based Additive of Formula (III)

Referring to FIG. 1B, citric acid (10 g, 52 mmol) and DEEA (6 g, 52 mmol) were placed in two neck round-bottom flask equipped with an air condenser. NaF (0.11 g, 2.6 mmol) was added to the reaction medium. The reaction was kept under stirring at 160° C. for one hour. The obtained orange sticky solid was collected and dried under vacuum for 48 h (12.26 g, 76.6% yield). The obtained product was used as is without any further purification. The chemical structure of the compound of formula (III) was confirmed by $^1$H and $^{13}$C NMR and FTIR.

$^1$H NMR (400 MHz, DMSO-d$_6$, δ): 1.0-1.07 (m, 6H), 2.6-2.71 (m, 6H), 2.72-2.93 (m, 4H), 3.47-3.55 (m, 2H), 8.29 (br s, NH). $^{13}$C NMR (100 MHz, DMSO-d$_6$, δ): 10.1, 11.2, 11.7, 35.2, 35.6, 42.5, 42.7, 42.8, 44.7, 47, 47.1, 48.7, 50.7, 71.8, 72.3, 72.5, 169.6, 171.9, 175.5, 177.4, 179.3.

The FTIR spectrum of the compound of formula (III) the —OH and —NH adsorption bands were found between 3000 and 3700 cm$^1$, while the C=O asymmetric stretching (O—C=O asym, str) and symmetric stretching (O—C=O sym, str) bands of carboxylic acid groups were located at 1778 and 1695 cm$^{-1}$, respectively. Moreover, the C=O stretching of the amide group (NH—C=O, str) was found at 1576 cm$^{-1}$. Also, the C—N stretching (C—N, str) was found at 1350 cm$^{-1}$ (FIG. 2).

Example 4: Thermogravimetric Analysis (TGA)

TGA was carried out to assess the thermal stability of the citric acid-based additive of formula (II) and (III). Referring now to FIG. 3, $T_{d,5}$% of compounds of formula (II) and (III) were found to be 105° C. and 163° C., respectively. Both compounds displayed thermal stability above 100° C., which is suitable for enhanced oil recovery application under reservoir conditions. The compound of formula (III) showed higher thermal stability relative to the compound of formula (II) which could be attributed to the chemical structure of the diamines. The compound of formula (III) contains ethyl substituents in the amine group, while the compound of formula (II) contains methyl substituents which might be less thermally stable. Further, the thermal stability of citric acid-based additive of formula (II) and (III) in sea water was studied. For this purpose, the citric acid-based additives of formula (II) and (III) were dissolved in sea water and placed in an oven at 100° C. for seven days. No precipitation was obtained, indicating their stability in saline water and under reservoir temperature.

Example 5: Wide-Angle X-Ray Diffraction (WXRD) Analysis

WXRD spectra were obtained to analyze morphologies of the citric acid-based additive of formula (II) and (III). Referring now to FIG. 4, the citric acid-based additive of formula (II) and (III) displayed amorphous morphologies as shown by the presence of broad peaks located at 2θ=18.2° with a d-spacing of 4.9 Å and 2θ=17.2° with a d-spacing of 5.2 Å for formula (II) and (III), respectively. Crystalline materials suffer from bad solubility in organic solvents and water, while amorphous materials tend to have good solubility due to the existing voids between molecules or polymer chains that allow solvents to penetrate and dissolve them. The presence of different hydrogen donors (NH and OH) and hydrogen acceptors (COOH, CONH) cause molecules to agglomerate or even react to form small oligomers, which display amorphous morphology like polymers. Referring to FIG. 4, the citric acid-based additive of formula (III) exhibited a peak at 2θ=26° with a d-spacing of 3.4 Å, resulting from the ethyl substitution that occupies more space and decreases the d-spacing between chains and molecules.

Example 6: Wettability Analysis

Effect of citric acid-based additive of formula (II) and (III) on the oil-wet carbonate rock sample was determined as a function of temperature and pressure. A concentration of 200 ppm of citric acid-based additive of formula (II) and (III) was used to prepare the fluid with the N-alkyl amide additive for the analysis. Referring to FIG. 5A, it can be witnessed that the addition of CA-based N-alkyl amide shows improvement in altering the wettability. Herein, the injected fluids alter the wettability from strongly oil-wet into the intermediate-wet. The addition of 200 ppm of a compound of formula (II) led to a contact angle reduction by 25% (from 160° to 120°) at the ambient condition. By increasing the temperature from 25° C. to 100° C., the contact angle reduction with a Δθ of 4.6° was obtained. Referring to FIG. 5B, the addition of 200 ppm of compound of formula (III) led to a contact angle reduction by 29% (from 160° to 113°) at the ambient condition. By increasing the temperature from 25° C. to 100° C., the contact angle reduction from 113.2° to 108.8° (Δθ≈5.7°) was obtained. Referring to FIGS. 5A & 5B, a marginal reduction in contact angle was observed upon increasing the pressure from 14.7 to 3000 psi. This shows that these N-alkyl amide compounds can preserve their characteristics at reservoir conditions (i.e., high temperature and high pressure) to alter the rock wettability.

Example 7: Oil Recovery Performance Analysis

Oil recovery analysis was carried out to evaluate the performance of fluids comprising citric acid-based additive of formula (II) and (III) on the carbonate rock samples for oil recovery. The analysis was carried out for two months, although they reached stable performance after 24 days. As a benchmark experiment, the imbibition experiment was also carried out with clean sea water to evaluate the performance of the different utilized fluids. To evaluate the performance of the citric acid-based additive of formula (II) and (III), the commonly known surfactants (i.e., CTAB and AOS) were also tested under the same conditions. Referring to FIG. 6, a fluid including sea water alone resulted in a maximum oil recovery of 29.1%. The fluid comprising 200 ppm citric acid-based additive of formula (II) displayed an oil recovery up to 41.3%, while at the same time, the recovery was increased up to 43.8% by using the fluid comprising 200 ppm citric acid-based additive of formula (III). Moreover, the fluid including the citric acid-based additive of formula (III) displayed an oil recovery of 43.8%, rising to 48.3% by increasing the concentration to 500 ppm. Additionally, the slight variation in the chemical structure of the N-alkyl amides can result in a trivial improvement in oil recovery. The citric acid-based additive of formula (II) and (III) at 500 ppm demonstrated an oil recovery of 44.7% and 48.3%, respectively, showing that replacing methyl groups with ethyl groups can increase the oil recovery by 8%. The initiation of oil recovery was observed to be very slow due to their oil-wet solid characteristics. The oil expels is initiated only after 10 hours of induction time. It was also observed that the recovery curve line for all the solutions followed the sea water case at the beginning. However, surfactant-based and citric acid-based additive solutions had a steep increment after a while (about 100 hours), reaching the plateau at about 576 hours.

The citric acid-based additive of formula (III) at 500 ppm enhanced the oil recovery by 19.2%, which is 70-92% higher than AOS and CTAB. Similarly, the citric acid-based additive of formula (II) at 500 ppm enhanced the oil recovery by 15.2%, which is 35-52% higher than AOS and CTAB. Although the recovery rate was faster (lesser induction time) in the case of AOS and CTAB, it ended up with a lower recovery with a quicker plateau as compared with the citric acid-based additive of formula (II) and (III). Therefore, the injected CA-based fluids are more effective in ultimate recovery and enhance oil recovery efficiency.

Generally, in chemical EOR, two classical mechanisms control the wettability and oil recovery performances. The first mechanism is the reduction of the oil-water interfacial tension (IFT), and the second mechanism is the wettability modification. As seen from the contact angle and IFT experiments (FIG. 5A, FIG. 5B, Table 1), the dominant mechanism for CA-based N-alkyl amides is the wettability modification since the CA-based N-alkyl amide's contribution to the wettability modification is more prevalent than the IFT reduction. While in the case of AOS and CTAB, the combined force of IFT reduction and wettability alteration would be considered as the mechanism for oil recovery.

TABLE 1

The oil-seawater IFT measurement as a function of concentration at 100° C.

| Sample | System | IFT (mN m$^{-1}$) at 100° C. | |
|---|---|---|---|
| | | CA-DMPA | CA-DEEA |
| 1 | Seawater | 20.15 | 20.15 |
| 2 | 10 ppm in SW | 19.95 | 19.91 |
| 3 | 50 ppm in SW | 19.75 | 19.56 |
| 4 | 100 ppm in | 19.61 | 19.45 |
| 5 | 200 ppm in | 19.35 | 19.23 |
| 6 | 500 ppm in | 19.12 | 19.01 |
| 7 | 500 ppm in | 18.98 | 18.88 |
| 8 | 500 ppm | 4.13 | |
| 9 | 500 ppm | 4.41 | |

The standard uncertainties are u(IFT) = 0.15 mN m$^{-1}$, u (fluids/surfactant conc.) = 2 ppm.

The presence of hydrophilic groups (i.e., NH, OH, and COOH) and hydrophobic chains in the CA-based structures increase the potential for the injected material to interact with the carbonate rocks and alter the contact angle more towards the water-wet. It reduces the oil adherence on the rock surface and improves the oil displacements. Furthermore, the adsorption of the CA-based fluids at the oil-water interface would reduce its capillary to some extent, which in fact, would increase the wetting phase pressure and that helps to spread out the wetting fluid on the surface or at the rock-oil-water interfaces and dislodges the oil droplet and pushes towards the outlet or production well [Iman Jafari and others, Scaling of counter-current imbibition recovery curves using artificial neural networks, Journal of Geophysics and Engineering, Volume 15, Issue 3, June 2018, Pages 1062-1070; Kondiparty K, Nikolov A, Wu S, Wasan D. Wetting and spreading of nanofluids on solid surfaces driven by the structural disjoining pressure: statics analysis and experiments. Langmuir. 2011 Apr. 5; 27(7):3324-35; McElfresh, Paul, Holcomb, David, and Daniel Ector. "Application of Nanofluid Technology to Improve Recovery in Oil and Gas Wells." Paper presented at the SPE International Oilfield Nanotechnology Conference and Exhibition, Noordwijk, The Netherlands, June 2012; Wasan D T, Nikolov A D. Spreading of nanofluids on solids. Nature. 2003 May 8; 423(6936):156-9, each of which is incorporated herein by reference in its entirety]. Moreover, AOS and CTAB are effective in reducing the IFT, but their oil recovery was less. This could be attributed to hydroxyl and carboxylic acid groups on CA-based N-alkyl amides. The presence of COOH groups allows interactions with the surface of the carbonate rocks through their surface oxygen and cationic sites. A computational study showed that molecules with short alkyl chains and carboxylic acid groups can get absorbed through perpendicular interactions directly on the carbonate surface, unlike molecules with long alkyl chains and weak function groups (as AOS and CTAB) [Raphael da Silva Alvim, Caetano Rodrigues Miranda, First-principles calculations of carboxylic acid adsorption on carbonate surfaces: Chain size and aqueous interface effects, Applied Surface Science, Volume 592, 2022, 153216, which is incorporated herein by reference in its entirety]. This absorption leads to altering the rock wettability and allows for higher recovery.

Figure 7:
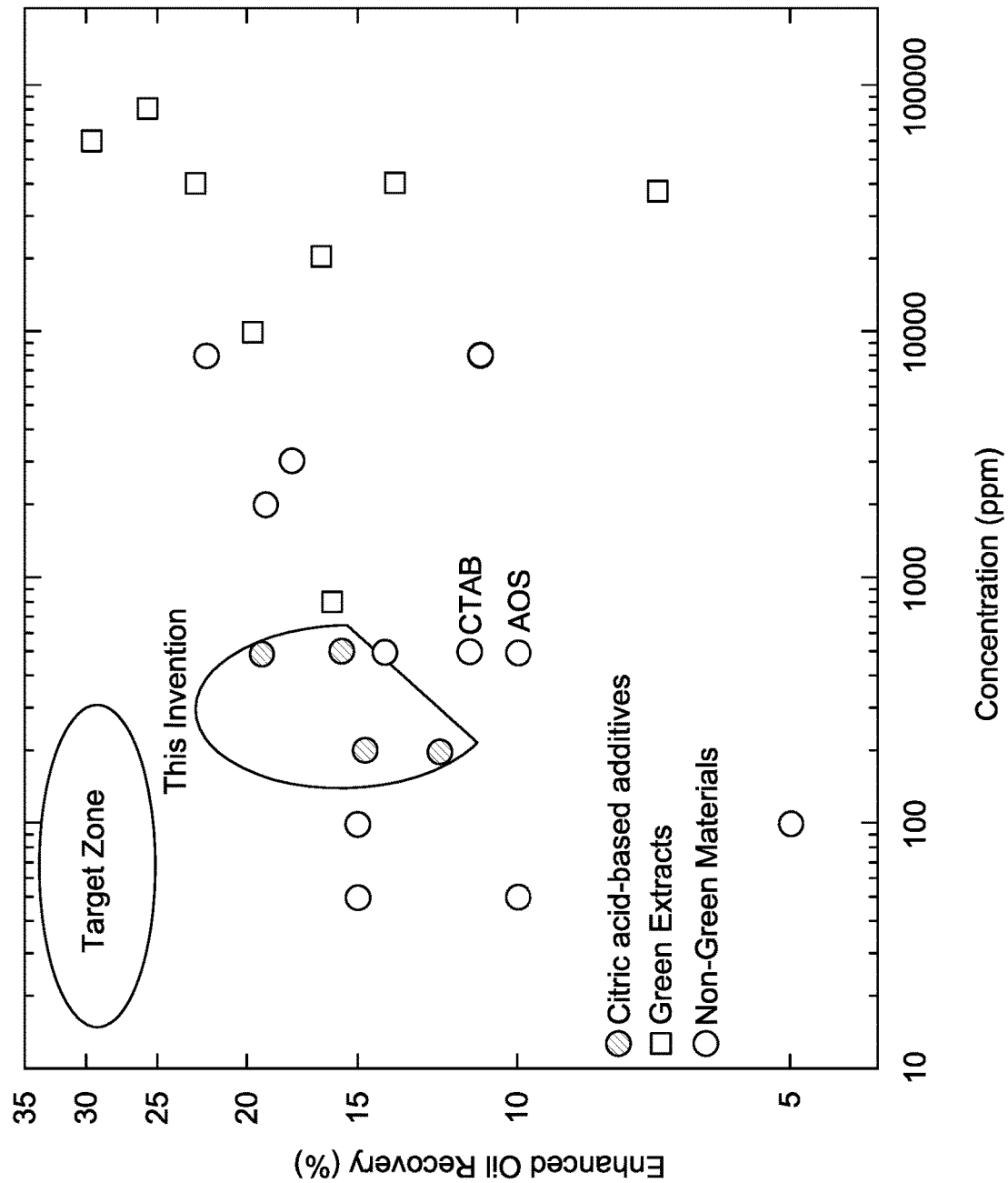
FIG. 7 shows a plot displaying relative oil recovery performance of non-green materials, green extracts, and the citric acid-based additives, according to certain embodiments.
Figure 8:
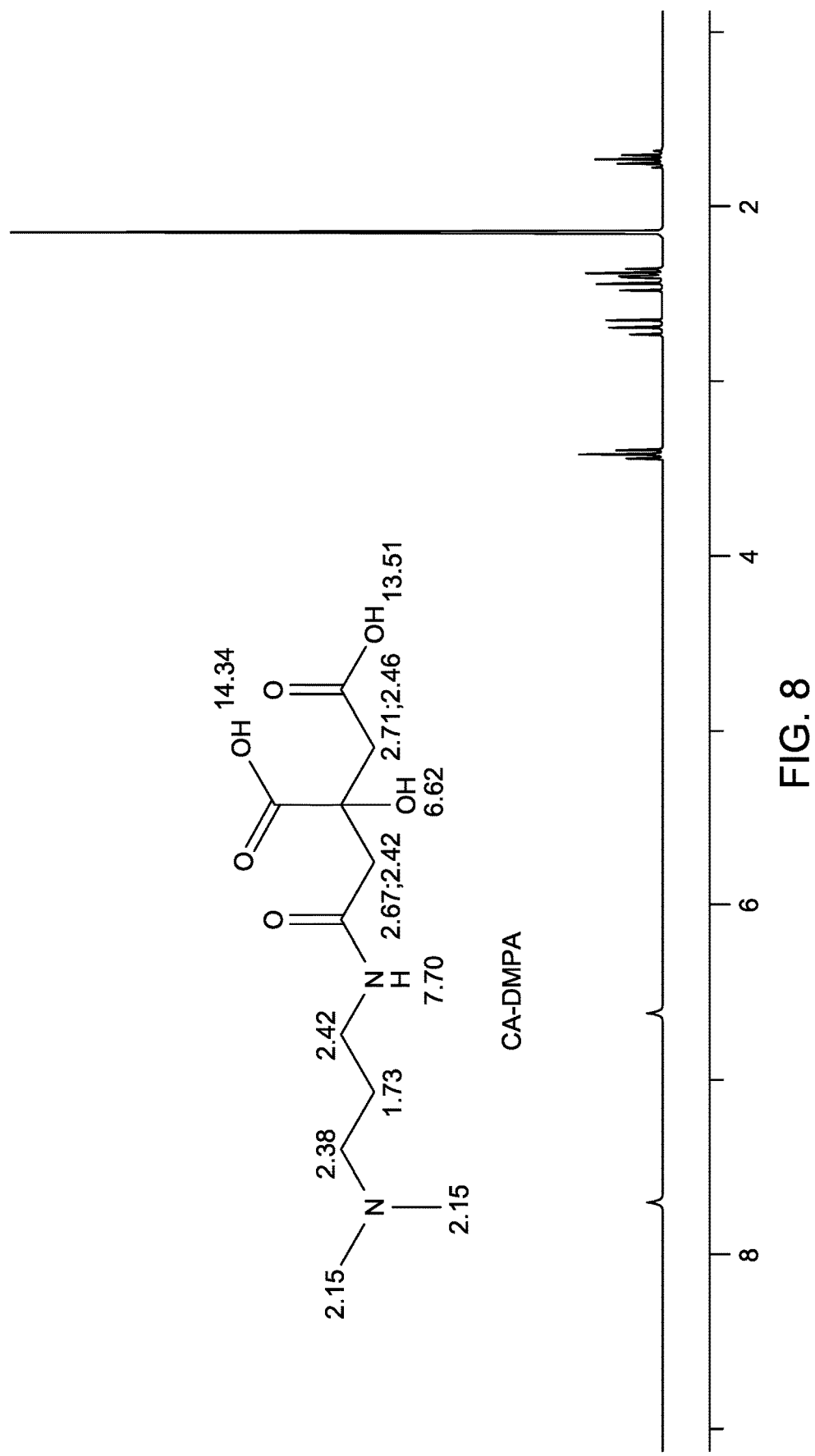
FIG. 8 depicts a predicted $^1$H nuclear magnetic resonance (NMR) spectra of 2-(2-((3-(dimethylamino)propyl)amino)-2-oxoethyl)-2-hydroxysuccinic acid (CA-DMPA), according to certain embodiments.

To further evaluate the oil recovery performance of the citric acid-based additive of formula (II) and (III), their performance was compared with non-green materials, such as graphene-based compounds and green extracts. Referring to FIG. 7, for industrial application, the target zone of performance may be defined with the lowest concentration and highest enhanced oil recovery. Interestingly, the graphene-based materials can achieve good oil recovery of 10 and 15% at a low solution concentration of 50 and 100 ppm, respectively [Luo, D., Wang, F., Zhu, J., Nanofluid of graphene-based amphiphilic Janus nanosheets for tertiary or enhanced oil recovery: High performance at low concentration, Proceedings of the National Academy of Science, 113, 2016, 7711, which is incorporated herein by reference in its entirety]. However, the green extracts can enhance the oil recovery when used at higher concentrations exceeding 10,000 ppm. The citric acid-based additive of formula (II) and (III) showed good, enhanced oil recovery at relatively low concentrations of 200 and 500 ppm.

The present disclosure describes the synthesis of two N-alkyl amides prepared from green citric acid (CA), by solvent-free condensation. These CA-based N-alkyl amides demonstrated good solubility in high-saline water and good thermal stability under reservoir conditions. The structure/property relationship between the compounds and their performance was described. The wettability of the oil-wet rock samples was altered from strongly oil-wet into the intermediate-wet (from 160° to 113°) with a diluted concentration of a compound of formula (III) (200 ppm). The CA-based N-alkyl amides resulted in cumulative oil recovery of 44.7%-48.3% with excellent stability at 100° C. and 3000 psi. Furthermore, the CA-based N-alkyl amides significantly enhanced (exceeded 90%) oil recovery relative to the commonly used AOS and CTAB surfactants. Additionally, their performance competed with organic and inorganic materials and performed better than previously reported green extracts. 19% of oil recovery increment was achieved using sustainable-based materials which is improved for the oil industry.

Numerous modifications and variations of the present disclosure are possible in light of the above teachings. It is therefore to be understood that within the scope of the appended claims, the invention may be practiced otherwise than as specifically described herein.

The invention claimed is:

1. A method of enhancing oil recovery from a carbonate reservoir containing a hydrocarbon mixture, comprising:
   injecting the carbonate reservoir with a sea-water solution comprising a citric acid-based additive having a formula (I) to displace the hydrocarbon mixture from the carbonate reservoir thereby forming a hydrocarbon mixture containing sea-water mixture; and
   separating the hydrocarbon mixture from the hydrocarbon mixture containing sea-water mixture to recover the hydrocarbon mixture;
wherein formula (I) is

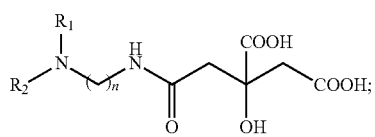

wherein $R_1$, and $R_2$ are each independently selected from the group consisting of an optionally substituted alkyl, an optionally substituted cycloalkyl, and an optionally substituted alkoxy, and wherein n is an integer from 2 to 8;

wherein the injecting is performed by injecting the sea-water solution into the carbonate reservoir through a wellbore using a chemical injection pump connected to the carbonate reservoir through an injection line disposed in the wellbore;

wherein the separating is performed by bringing the hydrocarbon mixture containing sea-water mixture to the surface:

wherein the citric acid-based additive is present in the sea-water solution at a concentration of 1 to 1000 parts per million (ppm) based on a total number of parts by weight of the sea-water solution; and wherein the citric acid-based additive is adsorbed on surfaces of the carbonate rocks in the carbonate reservoir.

2. The method of claim 1, wherein the sea-water solution is an aqueous solution having a salinity of from 20,000 to 300,000 ppm based on the total number of parts by weight of the sea-water solution.

3. The method of claim 2, wherein the sea-water solution is natural sea water having a salinity of from 55,000 to 60,000 ppm based on the total number of parts by weight of the natural sea water.

4. The method of claim 1, wherein $R_1$, and $R_2$ are each independently selected from the group consisting of methyl, ethyl, N-propyl, and isopropyl, and n is an integer from 2 to 4.

5. The method of claim 4, wherein the citric acid-based additive has a formula (II) or formula (III);

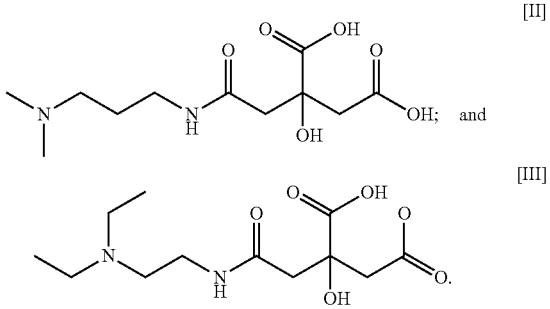

6. The method of claim 1, wherein the citric acid-based additive is present in the sea-water solution at a concentration of 200 ppm based on the total number of parts by weight of the sea-water solution.

7. The method of claim 1, having a cumulative oil recovery of 40 to 50% based on a total amount of hydrocarbon recovered from the carbonate reservoir at 100 degrees Celsius (° C.) and 3,000 pounds per square inch (psi).

8. The method of claim 1, wherein the carbonate reservoir has a temperature in a range of from 20 to 220° C., and a pressure in a range of 250 to 5,000 psi.

9. The method of claim 1, wherein a contact angle between a water droplet and a surface of hydrocarbon-wet carbonate rock in the carbonate reservoir is in a range of from 150 to 170 degrees (°) in the absence of the citric acid-based additive.

10. The method of claim 1, wherein after the injecting, a contact angle between a water droplet and a surface of hydrocarbon-wet carbonate rock in the carbonate reservoir is in a range of from 100 to 120° in the presence of the citric acid-based additive.

11. The method of claim 1, wherein the hydrocarbon mixture comprises at least one selected from the group consisting of crude oil, petroleum oil, shale oil, fossil oil, and biomass derived oil.

12. The method of claim 1, wherein the separating selected from the group consisting of an emulsion breaker, a water clarifier, a gravity oil separator, a plate separator, a coalescing plate separator, a separatory funnel, a settling tank, a centrifugal water-oil separator, a centrifugal settling device, a dewatering centrifuge, a decanter, and a skimming equipment.

13. The method of claim 1, wherein the sea-water solution further comprises at least one additive selected from the group consisting of an emulsifier, an anti-foaming agent, a fluid-loss additive, a viscosity modifier, a shale stabilizer, an alkali compound, a bridging agent, and a weighting agent.

14. The method of claim 13, wherein:
the emulsifier is selected from the group consisting of sodium lauryl sulfate (SLS), sodium dodecylbenzene sulfonate (SDBS), polyacrylate, tall oil fatty acid, and fatty amidoamine;
the anti-foaming agent is selected from the group consisting of polydimethylsiloxane, fatty acid ester, silicon dioxide, and vegetable oil;
the viscosity modifier is selected from the group consisting of a clay, a saccharide, a polysaccharide, a cellulose, an acrylate polymer and copolymer, and a polyvinyl polymer and copolymer;
the fluid-loss additive is selected from the group consisting of a starch, a starch derivative, a cellulose, and a cellulose derivative;
the shale stabilizer is selected from the group consisting of a sodium salt, and a sulfonated asphalt;
the alkali compound is selected from the group consisting of caustic soda and soda ash;
the bridging agent is selected from the group consisting of sodium borate, boric oxide, calcium carbonate, and magnesium oxide; and
the weighting agent is selected from the group consisting of barite and hematite.

15. The method of claim 1, further comprising:
preparing the citric acid-based additive having a formula (I) by melt condensation at a high temperature and without solvent:
mixing citric acid, a diamine, and a fluoride salt to form a mixture; and
heating the mixture at a temperature of at least from 150° C. to 200° C. for 4 to 96 hours thereby coupling an amine group of the diamine with a carboxylic acid group of the citric acid and drying to form the citric acid-based additive;
wherein a molar ratio of the citric acid and the diamine is in a range of 1:2 to 2:1.

16. The method of claim 15, wherein the fluoride salt is present in the mixture at a concentration of 0.1 to 1 wt. % based on a total weight of the mixture.

17. The method of claim 15, wherein the fluoride salt comprises at least one of calcium fluoride ($CaF_2$), sodium fluoride (NaF), and potassium fluoride (KF).

18. The method of claim 15, wherein the diamine has a formula (IV)

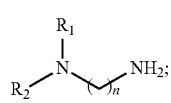 [IV]

wherein $R_1$, and $R_2$ are each independently selected from the group consisting of an optionally substituted alkyl, an optionally substituted cycloalkyl, and an optionally substituted alkoxy, and wherein n is an integer from 2 to 8.

19. The method of claim 15, wherein the diamine comprises at least one of N,N-dimethyl-1,3-propanediamine (DMPA), and N,N-diethylethylenediamine (DEEA).

20. The method of claim 15, wherein the heating is performed at a temperature of from 160° C. to 200° C. for 1 to 3 hours.

* * * * *